(12) United States Patent
Nakaminami et al.

(10) Patent No.: US 7,879,617 B2
(45) Date of Patent: Feb. 1, 2011

(54) METHOD, DEVICE AND APPARATUS FOR MEASURING THE CONCENTRATION OF CREATININE, AND METHOD, DEVICE AND APPARATUS FOR MEASURING THE AMOUNT OF SALT IN URINE USING THE SAME

(75) Inventors: Takahiro Nakaminami, Ehime (JP); Hiroaki Tachibana, Osaka (JP); Masato Suzuki, Osaka (JP)

(73) Assignee: Panasonic Corporation, Osaka (JP)

(*) Notice: Subject to any disclaimer, the term of this patent is extended or adjusted under 35 U.S.C. 154(b) by 0 days.

(21) Appl. No.: 12/683,134

(22) Filed: Jan. 6, 2010

(65) Prior Publication Data

US 2010/0105094 A1  Apr. 29, 2010

Related U.S. Application Data

(63) Continuation of application No. PCT/JP2009/002001, filed on May 7, 2009.

(30) Foreign Application Priority Data

May 9, 2008 (JP) ............................. 2008-123080
May 9, 2008 (JP) ............................. 2008-123081
May 9, 2008 (JP) ............................. 2008-123082

(51) Int. Cl.
*G01N 33/70* (2006.01)
*G01N 21/00* (2006.01)

(52) U.S. Cl. ......................................... 436/98; 436/164

(58) Field of Classification Search ....................... None
See application file for complete search history.

(56) References Cited

U.S. PATENT DOCUMENTS

| | | | |
|---|---|---|---|
| 3,705,013 A | 12/1972 | Dewhurst | |
| 4,215,197 A | 7/1980 | Tarbutton | |
| 4,812,399 A | 3/1989 | Mauck et al. | |
| 5,141,868 A | 8/1992 | Shanks et al. | |
| 5,466,575 A | 11/1995 | Cozzette et al. | |
| 2003/0027239 A1* | 2/2003 | Schaffar | 435/25 |
| 2005/0266574 A1 | 12/2005 | Kosaka | |

FOREIGN PATENT DOCUMENTS

| | | |
|---|---|---|
| JP | 54-151095 | 11/1979 |
| JP | 55-023998 | 2/1980 |
| JP | 63-033661 | 2/1988 |
| JP | 03-133396 | 6/1991 |
| JP | 07-248310 | 9/1995 |
| JP | 09-127126 | 5/1997 |
| JP | 2001-512692 | 8/2001 |
| JP | 2002-095498 | 4/2002 |
| JP | 2003-326172 | 11/2003 |
| JP | 2003-533679 | 11/2003 |
| JP | 2004-138408 | 5/2004 |
| JP | 2005-118014 | 5/2005 |
| JP | 2005-207949 | 8/2005 |
| JP | 2006-349412 | 12/2006 |
| JP | 2008-070346 | 3/2008 |
| WO | WO 99/007881 | 2/1999 |
| WO | WO 01/87300 A1 | 11/2001 |

OTHER PUBLICATIONS

Sullivan, M.X., et al., "A Highly Specific Test for Creatinine", The Journal of Biological Chemistry, 1958, pp. 530-534, vol. 233 No. 2.
Narayanan, S., et al., "Creatinine: A Review", Clin. Chem., 1980, pp. 1119-1126, vol. 26 No. 8.

* cited by examiner

*Primary Examiner*—Rebecca E. Prouty
*Assistant Examiner*—Paul C. Martin
(74) *Attorney, Agent, or Firm*—McDermott Will & Emery LLP

(57) ABSTRACT

A method for measuring the concentration of creatinine includes the steps of: (A) mixing a sample containing creatinine with a creatinine quantitative reagent including 1-methoxy-5-methylphenazinium in the absence of picric acid and any enzyme responsive to creatinine, to cause the creatinine to reduce the 1-methoxy-5-methylphenazinium; (B) electrochemically or optically measuring the amount of the 1-methoxy-5-methylphenazinium reduced in the step (A); and (C) determining the concentration of the creatinine contained in the sample from the amount of the reduced 1-methoxy-5-methylphenazinium measured in the step (B).

11 Claims, 19 Drawing Sheets

F I G. 9
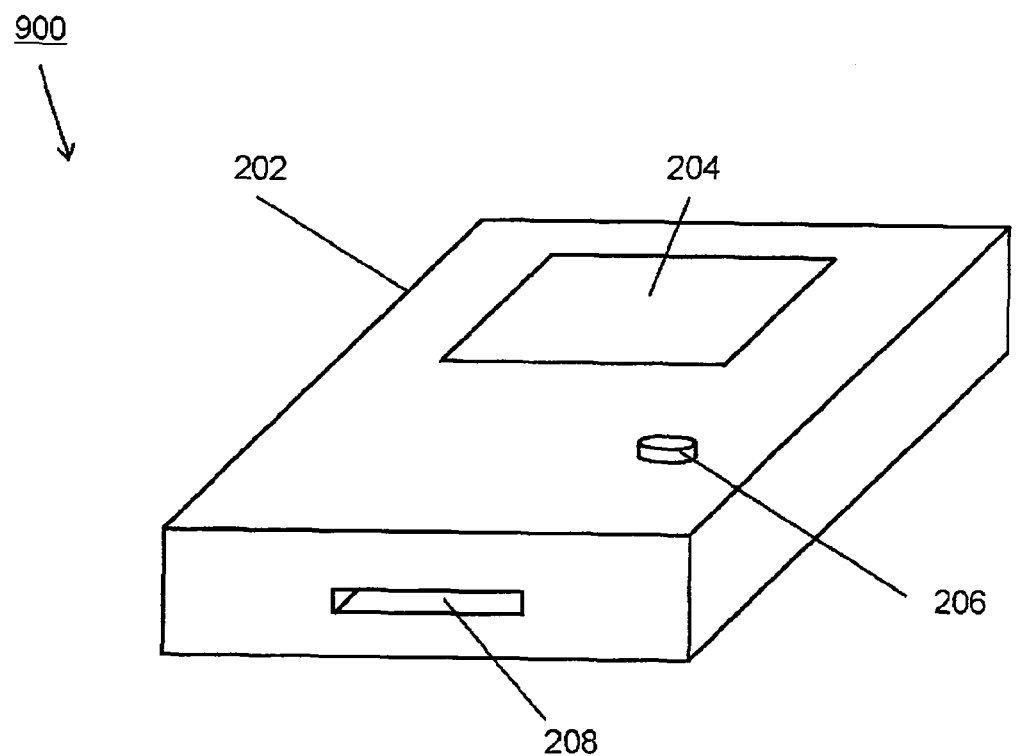

METHOD, DEVICE AND APPARATUS FOR MEASURING THE CONCENTRATION OF CREATININE, AND METHOD, DEVICE AND APPARATUS FOR MEASURING THE AMOUNT OF SALT IN URINE USING THE SAME

This application is a continuation of International Application No. PCT/JP2009/002001, whose international filing date is May 7, 2009 which in turn claims the benefit of Japanese Patent Application No. 2008-123080, Japanese Patent Application No. 2008-123081 and Japanese Patent Application No. 2008-123082 all of which were filed on May 9, 2008, the disclosures of which Applications are incorporated by reference herein. The benefit of the filing and priority dates of the International and Japanese Applications is respectfully requested.

TECHNICAL FIELD

The invention relates to a method, device, and apparatus for quantifying creatinine or salt contained in a sample.

BACKGROUND ART

Qualitative and quantitative detection of very small amounts of substances contained in biological and non-biological samples are commonly made in clinical examinations, diagnoses, analyses, self care, etc.

In such detection, an analyte in a sample is usually reacted with an indicator substance that reacts specifically with the analyte. The reaction product(s) or reaction composite(s) produced as a result of the reaction is/are detected by methods such as colorimetry (absorptiometric analysis), fluorometry, radiometry, chemiluminescent assay, electrochemical method, impedance method, quartz crystal microbalance method (QCM), surface plasmon resonance method (SPR), and thermal lens effect detection, to detect or quantify the analyte. A common indicator substance used in the detection or quantification of an analyte is 5-methylphenazinium methyl sulfate (chemical formula: $C_{14}H_{14}N_2O_4S$, hereinafter abbreviated as PMS). PMS reduced by the reaction with a specific analyte is detected by an electrochemical method or colorimetry to detect or quantify the analyte.

However, PMS is unstable and easily oxidized by light in an aqueous solution. Thus, it is known that the storage of such reagent solutions is difficult. To avoid the problem of storage, 1-methoxy-5-methylphenazinium methyl sulfate (chemical formula: $C_{15}H_{16}N_2O_5S$, hereinafter abbreviated as M-PMS), a derivative of PMS, was developed. M-PMS is a compound in which a methoxy group is introduced into the first position of PMS, and is very stable with respect to light.

The measurement of the concentration of creatinine contained in a sample is important in the fields of clinical chemistry and analytical chemistry. Since creatinine is a product of the endogenous metabolism of muscle, it is known that the amount of creatinine in urine reflects total muscle mass. Hence, it is believed that the amount of creatinine excretion in the urine of each individual in a day is usually constant and does not vary from day to day. As such, the amount of urinary creatinine may be used as a measure of the thickness of excreted urine. Also, the amount of creatinine in urine and blood increases/decreases due to uremia or decreased renal function. Thus, the measurement of the amount of creatinine in urine or blood permits determination of the presence or absence of uremia or decreased renal function.

A known method for measuring creatinine concentration is a method based on Jaffe reaction using an alkaline picrate solution. According to this method, the orange-red product formed by the reaction between picric acid and creatinine is spectroscopically measured (see, for example, PTL 1).

Another known method for measuring creatinine concentration is a method using an enzyme that reacts specifically with creatinine. An example of such an enzymatic method is a method of decomposing creatinine using creatinine deiminase. According to this method, the amount of ammonia produced by the decomposition of creatinine is measured based on the change in pH, potential, and the like to determine creatinine concentration (see, for example, PTL 2).

Another enzymatic method is a method of measuring creatinine concentration by carrying out the following reactions of formulas (1) to (3):

Creatinine+Water→Creatine    (1)

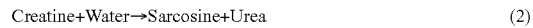

Creatine+Water→Sarcosine+Urea    (2)

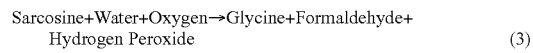

Sarcosine+Water+Oxygen→Glycine+Formaldehyde+ Hydrogen Peroxide    (3)

The enzymes used to catalyze the reactions of formulas (1) to (3) are creatinine amidohydrolase (creatininase), creatine amidinohydrolase (creatinase), and sarcosine oxidase or sarcosine dehydrogenase, respectively. Creatinine is quantified, for example, by a method of using a leuco pigment or the Trinder reagent together with a peroxidase to cause the hydrogen peroxide produced in formula (3) to give a color for spectroscopic quantification (see, for example, PTL 3). Also, another creatinine quantification method is a method of electrochemically oxidizing the hydrogen peroxide produced in formula (3) at an electrode to cause a current to flow and quantifying creatinine from the current (see, for example, PTLs 4 and 5).

Further, still another enzymatic method is a method of quantifying creatinine by carrying out the reactions of formula (1) and formula (2) and additionally carrying out the reaction between sarcosine and an electron mediator instead of the reaction of formula (3) (see, for example, PTLs 6 and 7).

PTL 6 discloses a creatinine biosensor including at least a pair of a working electrode and a counter electrode on a substrate, wherein a reagent solution is dried on the electrodes or on the substrate near the electrodes to immobilize the reagent. The reagent solution is prepared by dissolving creatininase, creatinase, sarcosine oxidase, and potassium ferricyanide (electron mediator) in a buffer solution of pH 7 to 8.5. It is also disclosed that a buffer solution pH of less than 7 or greater than 8.5 is not preferable since the enzyme activity decreases.

PTL 7 discloses quantifying creatinine by colorimetry or an electrochemical detection method using sarcosine oxidase and a mediator (electron mediator) encapsulated in cyclodextrin. Specifically, PTL 7 cites α-naphthoquinone (1,4-naphthoquinone) as an example of a mediator encapsulated in cyclodextrin, but discloses that mediators are not suitable for the enzymatic measurement of creatinine if they are not encapsulated in cyclodextrin.

Also, still another enzymatic method is a method of spectroscopically quantifying creatinine by carrying out the reactions of formula (1) and formula (2) and additionally carrying out the reaction between sarcosine and a tetrazolium indicator instead of the reaction of formula (3) (see, for example, PTL 8). PTL 8 discloses that the composition for creatinine quantification comprises a reagent mixture of creatinine hydrolase, creatine amidinohydrolase, sarcosine dehydrogenase, thiazolyl blue serving as the tetrazolium indicator, and potassium phosphate of pH 7.5.

Also, still another enzymatic method is a method of converting creatinine to glycine and formaldehyde by use of creatinine amidohydrolase, creatine amidinohydrolase, and sarcosine dehydrogenase, causing the produced formaldehyde to give a color with the aid of a color reagent, and quantifying creatinine from the absorbance (see, for example, PTL 9). PTL 9 discloses using a phosphate buffer solution of pH 7.5 and potassium ferricyanide serving as a reaction accelerator for promoting the formation of formaldehyde in addition to creatinine amidohydrolase, creatine amidinohydrolase, sarcosine dehydrogenase, and the color reagent.

Also, still another enzymatic method is a method of quantifying creatinine using an electrode on which a polymer that catalyzes the hydrolysis of creatinine, sarcosine oxidase, and a mediator are immobilized (see, for example, PTL 10). PTL 10 discloses using, for example, potassium ferricyanide, ferrocene, an osmium derivative, or phenazine methosulfate (PMS) as the mediator.

Still another method of creatinine concentration quantification is a method of using 1,4-naphthoquinone-2-potassium sulfonate (see, for example, PTL 11 and NPLs 1 to 3).

CITATION LIST

Patent Literature

PTL 1: U.S. Pat. No. 3,705,013
PTL 2: Japanese Laid-Open Patent Publication No. 2001-512692
PTL 3: Japanese Laid-Open Patent Publication No. Sho 62-257400
PTL 4: Japanese Laid-Open Patent Publication No. 2003-533679
PTL 5: U.S. Pat. No. 5,466,575
PTL 6: Japanese Laid-Open Patent Publication No. 2006-349412
PTL 7: Japanese Laid-Open Patent Publication No. 2005-118014
PTL 8: Japanese Laid-Open Patent Publication No. Sho 55-023998
PTL 9: Japanese Laid-Open Patent Publication No. Sho 54-151095
PTL 10: Japanese Laid-Open Patent Publication No. 2003-326172
PTL 11: Japanese Laid-Open Patent Publication No. Sho 63-033661

Non Patent Literature

NPL 1: Sullivan et al., "A Highly Specific Test for Creatinine", Journal of Biological Chemistry, 1958, Vol. 233, No. 2, p. 530-534
NPL 2: Narayanan et al., "Creatinine: A Review", Clinical Chemistry, 1980, Vol. 26, No. 8, p. 1119-1126
NPL 3: Cooper et al., "An Evaluation of Four Methods of Measuring Urinary Creatinine", 1961, Vol. 7, No. 6, P. 665-673

SUMMARY OF INVENTION

Technical Problem

However, the above-described conventional methods have the following problems.

In the method described in Patent Document 1, due to the influence of interferents such as amino acids including glycine, histidine, glutamine, and serine, proteins, sugars such as glucose, acetone, and bilirubin, it is difficult to accurately quantify creatinine in samples containing such substances, for example, in biological samples such as urine and blood. For example, amino acids and sugars such as glucose undesirably react with picric acid.

Also, in the method described in Patent Document 2, it is difficult to accurately quantify creatinine since the change in pH and potential is unstable.

Also, in the methods described in Patent Documents 2 to 10, if a sample contains an ion species such as salt or urea, the enzyme activity decreases due to enzyme denaturation. Thus, the reaction speed varies with the concentration of the ion species or urea contained in the sample. Therefore, in the quantification of creatinine in a sample containing an ion species or urea, for example, a biological sample such as urine or blood, the measurement result involves an error depending on the concentration of the ion species or urea contained in the sample.

Further, with respect to the methods of PTL 11 and NPL 1 using 1,4-naphthoquinone-2-potassium sulfonate, NPLs 2 and 3 have reported that the reproducibility of the results measured by these methods is very low.

In view of the above-described problems associated with conventional art, it is therefore a first object of the invention to provide a creatinine concentration measuring method, device and apparatus capable of measuring creatinine contained in a sample with good accuracy.

It is a second object of the invention to provide a salt measuring method, device and apparatus capable of quantifying the amount of salt contained in urine with good accuracy.

Solution to Problem

In order to solve the problems with conventional art, the method for measuring the concentration of creatinine according to the invention includes the steps of:

(A) mixing a sample containing creatinine with a creatinine quantitative reagent including 1-methoxy-5-methylphenazinium in the absence of picric acid and any enzyme responsive to creatinine, to cause the creatinine to reduce the 1-methoxy-5-methylphenazinium;

(B) electrochemically or optically measuring the amount of the 1-methoxy-5-methylphenazinium reduced in the step (A); and (C) determining the concentration of the creatinine contained in the sample from the amount of the reduced 1-methoxy-5-methylphenazinium measured in the step (B).

The method for measuring the amount of salt according to the invention includes the steps of:

(a) mixing urine, which is a sample, with a creatinine quantitative reagent including 1-methoxy-5-methylphenazinium in the absence of picric acid and any enzyme responsive to creatinine, to cause creatinine contained in the urine to reduce the 1-methoxy-5-methylphenazinium;

(b) electrochemically or optically measuring the amount of the 1-methoxy-5-methylphenazinium reduced in the step (a);

(c) measuring an electrical property of the urine; and (d) determining a value reflecting the amount of salt excreted into the urine from the amount of the reduced 1-methoxy-5-methylphenazinium measured in the step (b) and the electrical property measured in the step (c).

The device for measuring the concentration of creatinine according to the invention is a device used in the above-mentioned method for measuring the concentration of creatinine, and includes:

a sample holding space for holding a sample containing creatinine in the absence of picric acid and any enzyme responsive to creatinine;

a sample inlet for introducing the sample into the sample holding space, the sample inlet communicating with the sample holding space;

a creatinine quantitative reagent including 1-methoxy-5-methylphenazinium and disposed in the sample holding space; and two or more electrodes disposed in the sample holding space, or an optical measurement window disposed in the sample holding space.

The device for measuring the amount of salt according to the invention is a device used in the above-mentioned method for measuring the amount of salt, and includes:

a first sample holding space for holding urine, which is a sample, in the absence of picric acid and any enzyme responsive to creatinine;

a first sample inlet for introducing the urine into the first sample holding space, the first sample inlet communicating with the first sample holding space;

a creatinine quantitative reagent including 1-methoxy-5-methylphenazinium and disposed in the first sample holding space;

a second sample holding space for holding the urine;

a second sample inlet for introducing the urine into the second sample holding space, the second sample inlet communicating with the second sample holding space; and two or more electrodes disposed in the second sample holding space.

The apparatus for measuring the concentration of creatinine according to the invention includes:

a measuring device mounting port for mounting the above-mentioned device for measuring the concentration of creatinine;

a measurement system for electrochemically or optically measuring the amount of the 1-methoxy-5-methylphenazinium reduced by the creatinine in the sample holding space of the device for measuring the concentration of creatinine; and an arithmetic unit for determining the concentration of the creatinine contained in the sample from the amount of the reduced 1-methoxy-5-methylphenazinium measured by the measurement system.

Also, the apparatus for measuring the amount of salt according to the invention includes:

a measuring device mounting port for mounting the above-mentioned device for measuring the amount of salt;

a first measurement system for electrochemically or optically measuring the amount of the 1-methoxy-5-methylphenazinium reduced by the creatinine in the first sample holding space of the device for measuring the amount of salt;

a second measurement system for measuring an electrical property of the urine in the second sample holding space of the device for measuring the amount of salt; and an arithmetic unit for determining a value reflecting the amount of salt excreted into the urine from the amount of the reduced 1-methoxy-5-methylphenazinium measured by the first measurement system and the electrical property measured by the second measurement system.

It should be noted that 1-methoxy-5-methylphenazinium is unstable in the presence of a phosphate buffer. Therefore, when creatinine is reacted with 1-methoxy-5-methylphenazinium in the presence of a phosphate buffer, it is preferable to use an electrolyte salt of a monovalent anion together with the phosphate buffer.

ADVANTAGEOUS EFFECTS OF INVENTION

According to the method for measuring the concentration of creatinine of the invention, creatinine contained in a sample is quantified with good accuracy in the absence of picric acid and any enzyme responsive to creatinine.

BRIEF DESCRIPTION OF DRAWINGS

FIG. 9 is a perspective view showing the appearance of an apparatus for measuring the amount of salt in the same embodiment;

DESCRIPTION OF EMBODIMENTS

Figure 1:
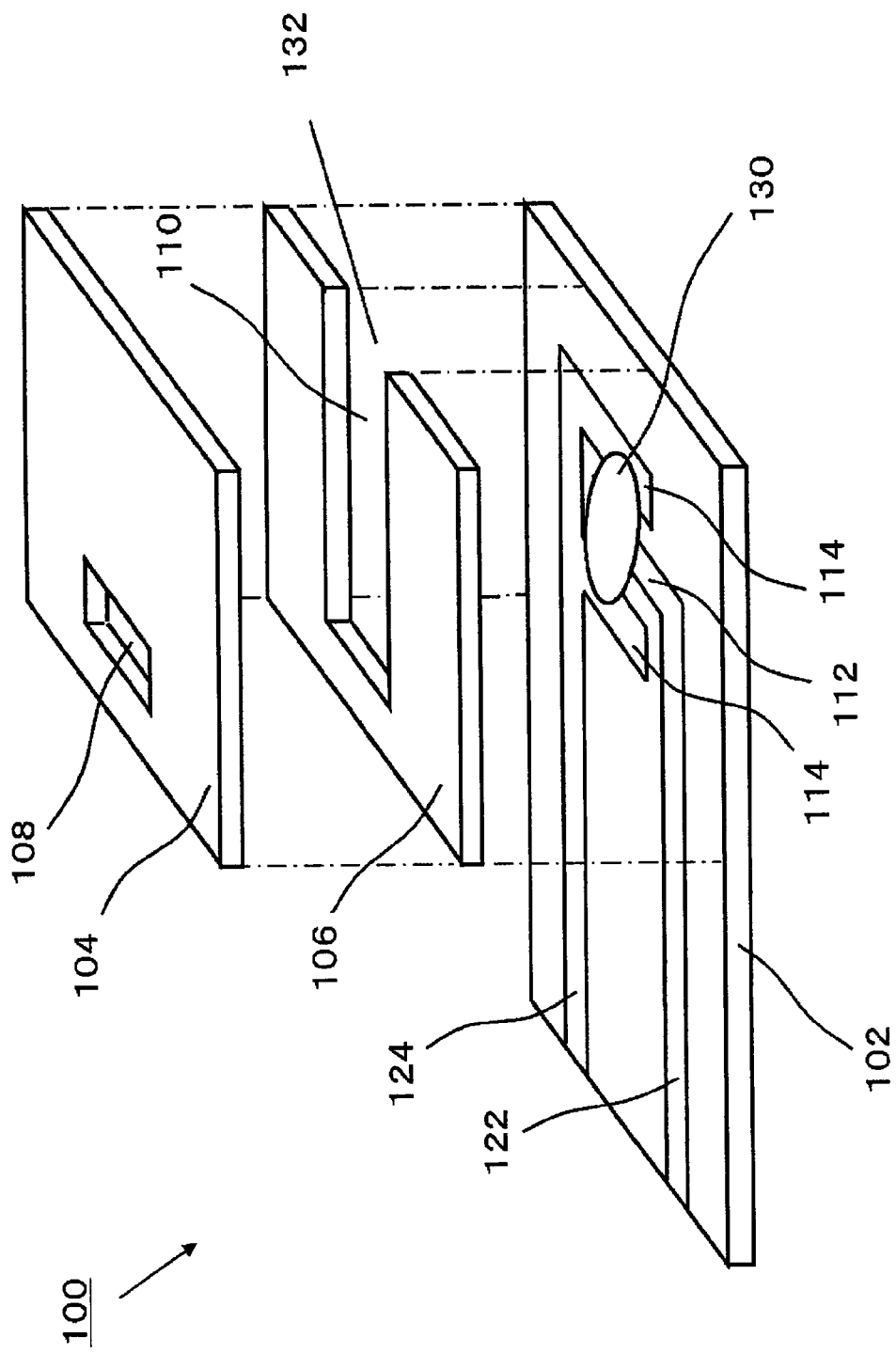
FIG. 1 is an exploded perspective view showing the structure of a device for measuring creatinine concentration in Embodiment 1 of the invention.

The inventors have found that creatinine directly reacts with 1-methoxy-5-methylphenazinium. In this reaction, creatinine reacts with 1-methoxy-5-methylphenazinium, despite the absence of picric acid and any enzyme responsive to creatinine (e.g., creatinine amidohydrolase). As a result, the amounts of creatinine and 1-methoxy-5-methylphenazinium decrease, and an oxidation product of creatinine and reduced 1-methoxy-5-methylphenazinium are formed.

The invention is based on the above finding and is characterized in that 1-methoxy-5-methylphenazinium is used as a creatinine quantitative reagent or an effective component of a reagent composition. 1-methoxy-5-methylphenazinium is usually present in the form of a salt. For example, in the state of a solid, 1-methoxy-5-methylphenazinium forms a salt with a counter anion. In a solution, a salt of 1-methoxy-5-methylphenazinium is ionized, and 1-methoxy-5-methylphenazinium is present in the form of a solvated cation.

Examples of salts of 1-methoxy-5-methylphenazinium used in the invention include 1-methoxy-5-methylphenazinium methyl sulfate and 1-methoxy-5-methylphenazinium chloride. Among them, 1-methoxy-5-methylphenazinium methyl sulfate (chemical formula: $C_{15}H_{16}N_2O_5S$, hereinafter abbreviated as M-PMS) represented by the following structural formula (4) is preferable.

[Chemical Formula 1]

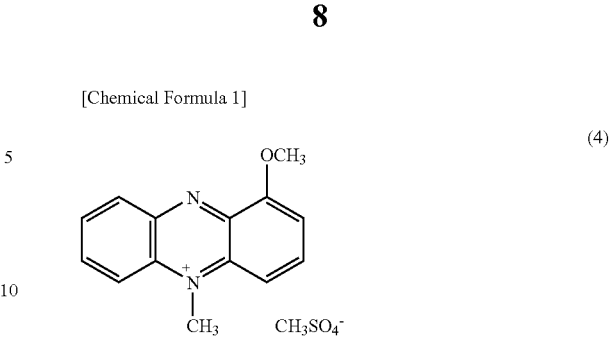

(4)

The method for measuring the concentration of creatinine according to the invention includes the steps of:

(A) mixing a sample containing creatinine with a creatinine quantitative reagent including 1-methoxy-5-methylphenazinium in the absence of picric acid and any enzyme responsive to creatinine, to cause the creatinine to reduce the 1-methoxy-5-methylphenazinium;

(B) electrochemically or optically measuring the amount of the 1-methoxy-5-methylphenazinium reduced in the step (A); and (C) determining the concentration of the creatinine contained in the sample from the amount of the reduced 1-methoxy-5-methylphenazinium measured in the step (B).

According to this method, in the absence of picric acid and any enzyme responsive to creatinine, creatinine directly reacts with 1-methoxy-5-methylphenazinium, unlike conventional measurement methods. Therefore, the reaction proceeds without being affected by interferents including ion species such as salt, urea, amino acids, and sugars. Hence, even in the case of using a biological sample such as urine or blood, it is possible to quantify creatinine contained in the sample with a better accuracy than that of conventional measuring methods.

In the step (A), the sample may be mixed with a buffer. Examples of buffers include phosphate buffers, citrate buffers, phthalate buffers, acetate buffers, and an MES buffer.

In the step (A), the sample is preferably mixed with a phosphate buffer so that the pH of the sample is adjusted to preferably 5 to 10, and more preferably 6 to 7.

This increases the speed of the direct reaction between creatinine and 1-methoxy-5-methylphenazinium (the reduction of 1-methoxy-5-methylphenazinium by creatinine), thereby allowing a reduction in measurement time. This will be specifically described in an Example referring to FIG. 16.

Examples of phosphate buffers include dipotassium hydrogen phosphate, potassium dihydrogen phosphate, disodium hydrogen phosphate, sodium dihydrogen phosphate, phosphoric acid, and hydrates thereof.

The phosphate buffer is preferably composed of a hydrogen phosphate and a dihydrogen phosphate, and is more preferably composed of dipotassium hydrogen phosphate and potassium dihydrogen phosphate. By dissolving such phosphates in a sample, the pH of the sample is easily adjusted to 6 to 7.

In the step (A), the concentration of the phosphate buffer (concentration of phosphorus atoms) in the sample is preferably 5 to 1000 mM, and more preferably 5 to 500 mM. The inventors have found that as the concentration of the phosphate type ion increases, the speed of the reaction between creatinine and 1-methoxy-5-methylphenazinium increases. If the concentration of the phosphate buffer is 5 mM or more, a sufficient reaction speed may be obtained. Also, 1000 mM is the upper limit of the solubility of phosphate buffers capable of adjusting the pH of a sample to 6 to 7.

In the step (A), the sample may be mixed with an electrolyte salt of a monovalent anion. The presence of the monovalent anion in the sample stabilizes 1-methoxy-5-methylphenazinium even in the presence of a phosphate buffer. It is therefore possible to quantify creatinine contained in a sample with good reproducibility.

The monovalent anion for such an electrolyte salt may be selected from the group consisting of a chloride ion, a nitrate ion, and a methyl sulfate ion.

Examples of electrolyte salts of monovalent anions include lithium chloride, sodium chloride, potassium chloride, lithium nitrate, sodium nitrate, potassium nitrate, lithium methyl sulfate, sodium methyl sulfate, and potassium methyl sulfate. Of such electrolyte salts of monovalent anions, the composition of the creatinine quantitative reagent may contain two or more electrolyte salts.

In the step (A), it is preferable that the concentration of 1-methoxy-5-methylphenazinium in the sample be 1 to 100 mM, and that the concentration of the monovalent anion be 5 to 1000 mM.

In the step (A), the molar concentration of the phosphate buffer (the molar concentration of phosphorus atoms) contained in the sample is preferably equal to or less than half the total of the molar concentration of the monovalent anion and the molar concentration of 1-methoxy-5-methylphenazinium methyl sulfate.

This further stabilizes 1-methoxy-5-methylphenazinium methyl sulfate in the sample. It is thus possible to quantify creatinine contained in the sample with a better reproducibility.

Accordingly, it is preferable to use the creatinine quantitative reagent as a creatinine quantitative reagent composition containing 1-methoxy-5-methylphenazinium, a phosphate buffer, and an electrolyte salt of a monovalent anion.

The amount of the phosphate buffer (the number of moles of phosphorus atoms) contained in the reagent composition is preferably equal to or less than half the total of the amount of the electrolyte salt of the monovalent anion (the number of moles of the monovalent anion) and the amount of 1-methoxy-5-methylphenazinium (the number of moles).

When the amount of the reduced 1-methoxy-5-methylphenazinium is electrochemically measured, for example, the step (B) includes:

(D) bringing the sample into contact with two or more electrodes and applying a voltage between the two electrodes; and (E) detecting the current value or the amount of electric charge flowing between the two electrodes.

Also, the step (C) includes the step of determining the concentration of creatinine contained in the sample from the current value or the amount of electric charge detected in the step (E).

In this case, the concentration of creatinine contained in a sample is electrochemically determined with ease.

When the amount of the reduced 1-methoxy-5-methylphenazinium is optically measured, for example, the step (B) includes the steps of:

(F) irradiating the sample with light; and (G) detecting the light transmitted through the sample or the light reflected by the sample.

Also, the step (C) includes the step of determining the concentration of creatinine contained in the sample from the intensity of the transmitted light or the reflected light detected in the step (G).

In this case, the concentration of creatinine contained in a sample is optically determined with ease.

The method for measuring the amount of salt according to the invention uses urine as a sample, and includes the following steps (c) and (d) in addition to the steps (A) and (B) of the above-mentioned method for measuring creatinine concentration.

That is, the method for measuring the amount of salt according to the invention includes the steps of:

(a) mixing urine, which is a sample, with a creatinine quantitative reagent including 1-methoxy-5-methylphenazinium in the absence of picric acid and any enzyme responsive to creatinine, to cause creatinine contained in the urine to reduce the 1-methoxy-5-methylphenazinium;

(b) electrochemically or optically measuring the amount of the 1-methoxy-5-methylphenazinium reduced in the step (a);

(c) measuring an electrical property of the urine; and (d) determining a value reflecting the amount of salt excreted into the urine from the amount of the reduced 1-methoxy-5-methylphenazinium measured in the step (b) and the electrical property measured in the step (c).

It is preferable to perform the step (c) before the step (a), for example, after the step (b) and before the step (d).

An electrical property of urine in which no creatinine quantitative reagent is dissolved reflects the concentration of electrolyte contained in the urine. The concentration of electrolyte contained in the urine correlates with the concentration of salt contained in the urine. Components such as salt are affected by water intake, sweating, and the like, so they are concentrated or diluted before being excreted into the urine. A random urine sample is a urine sample collected randomly irrespective of daytime or nighttime. The concentration of urinary components, such as salt in a random urine sample fluctuates due to the influence of concentration and dilution of urine.

On the other hand, the amount of creatinine produced is dependent on the amount of muscle, as described above. It is thus known that the amount of urinary creatinine excretion per unit time is constant. Even in the case of using a random urine sample, the influence of the concentration and dilution of urine may be corrected, for example, by obtaining the ratio of the concentration of a measured urinary component to the creatinine concentration (the ratio of urinary component/creatinine).

The value measured in the step (b) reflects the creatinine concentration with high accuracy and good reproducibility. The electrical property in the step (c) reflects the salt concentration. Thus, in the method for measuring the amount of salt according to the invention, the influence of the concentration and dilution of urine is corrected with high accuracy and good reproducibility. It is therefore possible to obtain a value that properly reflects the amount of urinary salt excretion.

Examples of electrical properties of urine include resistance, conductivity, impedance, voltage (or current) signal produced in response to input current (or voltage) signal, and phase difference between the phase of input AC signal and the phase of output AC signal.

Examples of values reflecting the amount of urinary salt excretion determined in the step (d) include the amount of salt per unit amount of creatinine, the amount of urinary salt excretion per unit time (e.g., 1 day), and the amount of salt intake per unit time (e.g., 1 day).

The device for measuring creatinine concentration according to the invention (hereinafter also referred to as measuring device A) includes:

a sample holding space for holding a sample containing creatinine in the absence of picric acid and any enzyme responsive to creatinine;

a sample inlet for introducing the sample into the sample holding space, the sample inlet communicating with the sample holding space; and a creatinine quantitative reagent including 1-methoxy-5-methylphenazinium and disposed in the sample holding space. This device is used in the above-mentioned method for measuring creatinine concentration.

With the measuring device A, creatinine directly reacts with 1-methoxy-5-methylphenazinium in the sample holding space in the absence of picric acid and any enzyme responsive to creatinine, unlike conventional measuring devices. Therefore, the reaction proceeds without being affected by interferents including ion species such as salt, urea, amino acids, sugars, and acetone. Hence, even in the case of using a biological sample such as urine or blood, it is possible to quantify creatinine contained in the sample with a better accuracy than that of conventional measuring devices.

The measuring device A may include a buffer such as a phosphate buffer in the sample holding space. Also, it may further include an electrolyte salt of a monovalent anion in the sample holding space. When a monovalent anion, 1-methoxy-5-methylphenazinium, and a phosphate buffer coexist in the sample holding space, 1-methoxy-5-methylphenazinium is stabilized. It is thus possible to quantify creatinine contained in a sample with good reproducibility.

The measuring device A may further include two or more electrodes in the sample holding space.

In this case, the concentration of creatinine contained in a sample is electrochemically determined with ease.

The measuring device A may further include an optical measurement window disposed in the sample holding space.

In this case, the concentration of creatinine contained in a sample is optically determined with ease.

The device for measuring the amount of salt according the invention (hereinafter also referred to as measuring device B) includes:

a first sample holding space for holding urine, which is a sample, in the absence of picric acid and any enzyme responsive to creatinine;

a first sample inlet for introducing the urine into the first sample holding space, the first sample inlet communicating with the first sample holding space;

a creatinine quantitative reagent including 1-methoxy-5-methylphenazinium and disposed in the first sample holding space;

a second sample holding space for holding the urine;

a second sample inlet for introducing the urine into the second sample holding space, the second sample inlet communicating with the second sample holding space; and two or more electrodes disposed in the second sample holding space. This device is used in the above-mentioned method for measuring the amount of salt.

The measuring device B may measure the amount of reduced 1-methoxy-5-methylphenazinium which accurately reflects creatinine concentration and an electrical property of urine which reflects salt concentration. By using the amount of reduced 1-methoxy-5-methylphenazinium and the electrical property, the influence of concentration and dilution of urine may be corrected with good accuracy. It is thus possible to obtain a value which properly reflects the amount of urinary salt excretion.

The measuring device B may further include two or more electrodes in the first sample holding space.

In this case, a value which properly reflects the amount of urinary salt excretion is electrochemically determined with ease.

The apparatus for measuring creatinine concentration according to the invention (hereinafter also referred to as measuring apparatus A) includes:

a measuring device mounting port for mounting the measuring device A;

a measurement system for electrochemically or optically measuring the amount of the 1-methoxy-5-methylphenazinium reduced by the creatinine in the sample holding space of the measuring device A; and an arithmetic unit for determining the concentration of the creatinine contained in the sample from the amount of the reduced 1-methoxy-5-methylphenazinium measured by the measurement system.

The measuring apparatus A may electrochemically or optically measure the concentration of creatinine contained in a sample with high accuracy and good reproducibility by using the measuring device A.

When the amount of the reduced 1-methoxy-5-methylphenazinium is optically measured in the sample holding space, the measurement system includes, for example, a light source for emitting light to the sample holding space of the measuring device A, and a light receiver for detecting the light transmitted through the sample holding space or the light reflected by the sample holding space. In this case, the arithmetic unit determines the concentration of the creatinine contained in the sample from the intensity of the transmitted light or the reflected light detected by the light receiver.

With this configuration, using the measuring device A, the concentration of creatinine contained in a sample is optically determined with ease.

The light source emits light including such a wavelength that the absorption intensity changes depending on the reaction between 1-methoxy-5-methylphenazinium and creatinine. Examples of light sources include an LED and a laser.

When the measuring device A further includes two or more electrodes in the sample holding space, the measurement system includes, for example, a voltage application unit for applying a voltage between the two electrodes, and a detector for detecting the current value or the amount of electric charge flowing between the two electrodes. In this case, the arithmetic unit determines the concentration of the creatinine contained in the sample from the current value or the amount of electric charge detected by the detector.

With this configuration, using the measuring device A, the concentration of creatinine contained in a sample is electrochemically determined with ease.

The apparatus for measuring the amount of salt according to the invention (hereinafter also referred to as measuring apparatus B) includes:

a measuring device mounting port for mounting the measuring device B;

a first measurement system for electrochemically or optically measuring the amount of the 1-methoxy-5-methylphenazinium reduced by the creatinine in the first sample holding space of the measuring device B;

a second measurement system for measuring an electrical property of the urine in the second sample holding space of the measuring device B; and an arithmetic unit for determining a value reflecting the amount of salt excreted into the urine from the amount of the reduced 1-methoxy-5-methylphenazinium measured by the first measurement system and the electrical property measured by the second measurement system.

The measuring apparatus B may electrochemically or optically measure a value reflecting the amount of urinary salt excretion with high accuracy and good reproducibility by using the measuring device B.

When the amount of the reduced 1-methoxy-5-methylphenazinium is optically measured in the first sample holding space, the measurement system includes, for example, a light source for emitting light to the first sample holding space, and a light receiver for detecting the light transmitted through the first sample holding space or the light reflected by the sample holding space. In this case, the arithmetic unit determines the amount of the reduced 1-methoxy-5-methylphenazinium from the intensity of the transmitted light or the reflected light detected by the light receiver.

With this configuration, using the measuring device B, a value reflecting the amount of urinary salt excretion is optically determined with ease.

When the measuring device B further includes two or more electrodes in the first sample holding space, the measurement system includes, for example, a voltage application unit for applying a voltage between the two electrodes, and a detector for detecting the current value or the amount of electric charge flowing between the two electrodes. In this case, the arithmetic unit determines the amount of the reduced 1-methoxy-5-methylphenazinium from the current value or the amount of electric charge detected by the detector.

With this configuration, using the measuring device B, a value reflecting the amount of urinary salt excretion is electrochemically determined with ease.

Examples of samples include aqueous solutions and body fluids such as blood, blood serum, blood plasma, urine, interstitial fluid, lymph, and saliva. In particular, urine is a very effective sample for non-invasive, daily healthcare at home. Since the concentration of ion species and urea in these body fluids is relatively high, the invention is very effective.

With respect to the two or more electrodes of the invention, the materials thereof preferably include at least one of gold, platinum, palladium, alloys and mixtures thereof, and carbon. These materials are chemically and electrochemically stable, thus realizing stable measurements. As a third electrode, it is also possible to use an electrode with stable potential, for example, a reference electrode such as an Ag/AgCl or saturated calomel electrode, in combination with the above-mentioned two electrodes. If the potential of one of the two electrodes is regulated relative to the third electrode, the potential for measurement becomes stable, which is preferable. Also, as the other electrode of the two electrodes, for example, an Ag/AgCl or saturated calomel electrode may be used.

In the measuring devices A and B, it is preferable that the creatinine quantitative reagent be stored in a dry state and dissolved by a sample when the sample is introduced in the sample holding space.

In the measuring devices A and B, it is particularly preferable that M-PMS, the electrolyte salt of the monovalent anion, and the phosphate buffer be stored in a dry state and dissolved by a sample when the sample is introduced in the sample holding space.

For example, a porous carrier made of glass fibers, filter paper, or the like is impregnated with a solution containing a creatinine quantitative reagent, and dried to dispose the creatinine quantitative reagent on the carrier. The carrier is then disposed on a portion to come into contact with a sample. Also, a solution containing a creatinine quantitative reagent may be directly applied to a portion of a wall of a measuring device to come into contact with a sample, and dried to dispose the creatinine quantitative reagent on the wall. The solution containing a creatinine quantitative reagent may include a buffer and an electrolyte salt of a monovalent anion.

It is preferable that the measuring devices A and B be detachably mounted in the measuring device mounting ports of the measuring apparatuses A and B, respectively. Also, in the case of using biological liquids such as urine and blood, in particular, it is preferable for hygienic reasons that the measuring devices A and B be disposable.

Embodiments of the present invention are hereinafter described with reference to drawings.

Embodiment 1

A device 100 for measuring creatinine concentration according to Embodiment 1 of the invention is described with reference to FIG. 1. FIG. 1 is an exploded perspective view showing the structure of the measuring device 100.

The measuring device 100 is used in a method for electrochemically quantifying the concentration of creatinine contained in a sample. The measuring device 100 is composed of an insulating first substrate 102 and an insulating second substrate 104 with an air vent 108 which are combined so as to sandwich an insulating spacer 106 with a slit 110. The first substrate 102, the second substrate 104, and the spacer 106 are made of, for example, polyethylene terephthalate.

The first substrate 102 has a first electrode 112, a second electrode 114, a first lead 122 electrically connected to the first electrode 112, and a second lead 124 electrically connected to the second electrode 114. Formed on the first electrode 112 and the second electrode 114 is a reagent layer 130 containing a creatinine quantitative reagent. The dimensions of the first substrate 102 may be suitably set; for example, the width is approximately 7 mm, the length is approximately 30 mm, and the thickness is approximately 0.7 mm.

Next, the method for producing the measuring device 100 is described.

First, palladium is sputtered onto the first substrate 102 with a resin mask of an electrode pattern thereon, to form the first electrode 112, the second electrode 114, the first lead 122, and the second lead 124. The first electrode 112 and the second electrode 114 are electrically connected to the terminals of an apparatus for measuring creatinine concentration, which will be described below, by the first lead 122 and the second lead 124, respectively.

Next, a given amount of an aqueous solution of M-PMS, potassium dihydrogen phosphate, dipotassium hydrogen phosphate, and optionally an electrolyte salt of a monovalent anion is dropped on the first electrode 112 and the second electrode 114 formed on the first substrate 102 by using a microsyringe or the like. As the electrolyte salt of a monovalent anion, it is preferable to use, for example, sodium methyl sulfate, which is a sodium salt of a methyl sulfate ion (monovalent anion). Thereafter, the first substrate 102 is left for drying in an environment at room temperature to approximately 30° C., to form the reagent layer 130.

The concentration and amount of the reagent containing aqueous solution to be applied thereto may be selected depending on the characteristics and size of the necessary device. For example, the concentration of M-PMS in the reagent containing aqueous solution is approximately 10 mM, and the dropping amount of the reagent containing aqueous solution is approximately 1.4 µL. Also, the area of the region on which the reagent layer 130 is formed may be suitably selected in view of the solubility and the like of the reagent in the sample, and the area is, for example, approximately 3 $mm^2$.

Next, the first substrate 102 with the electrodes and the reagent layer 130 formed thereon is combined with the spacer 106 and the second substrate 104. Adhesive is applied to the portions of the first substrate 102, the spacer 106, and the second substrate 104 to be bonded. They are laminated, pressed, and allowed to stand for bonding. Instead of this method, it is also possible to combine them without applying adhesive and then thermally or ultrasonically bond the bonding portions by using a commercially available welding machine.

When the first substrate 102, the spacer 106, and the second substrate 104 are combined, a space is formed by the slit 110 of the spacer 106 between the first substrate 102 and the second substrate 104, and this space serves as a sample holding space. Also, the opening of the slit 110 serves as a sample inlet 132.

Figure 2:
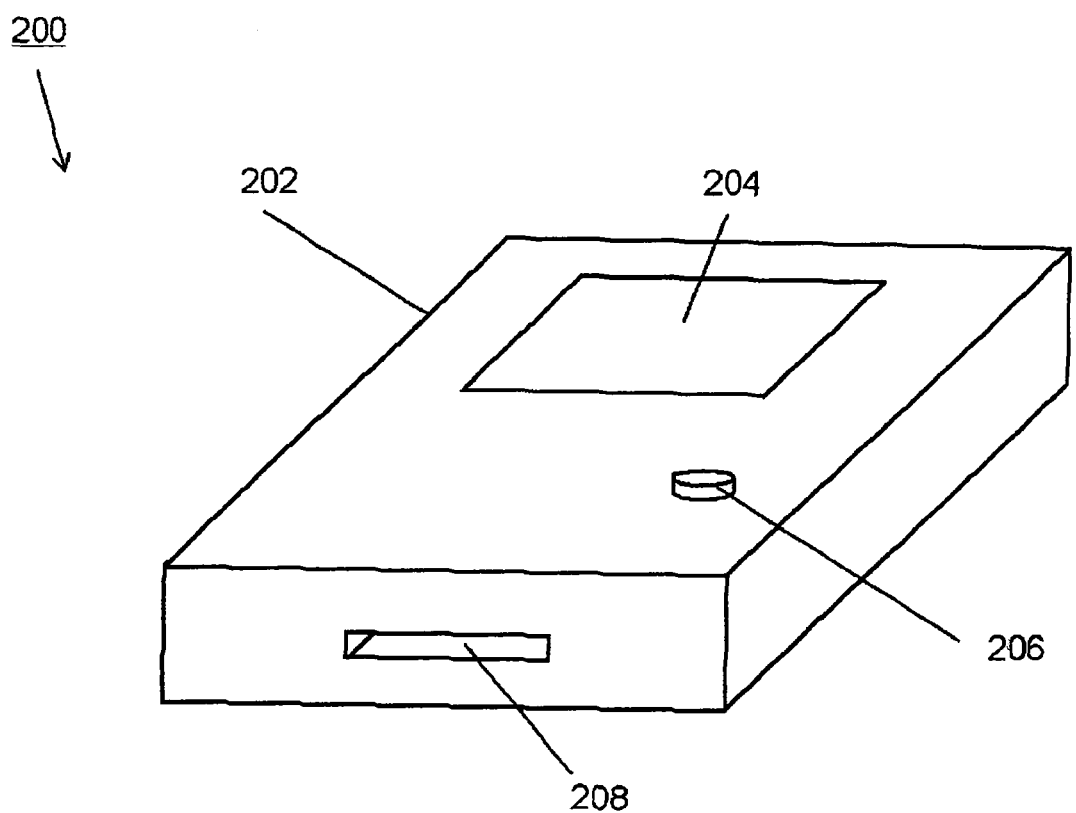
FIG. 2 is a perspective view showing the appearance of an apparatus for measuring creatinine concentration in the same embodiment.
Figure 3:
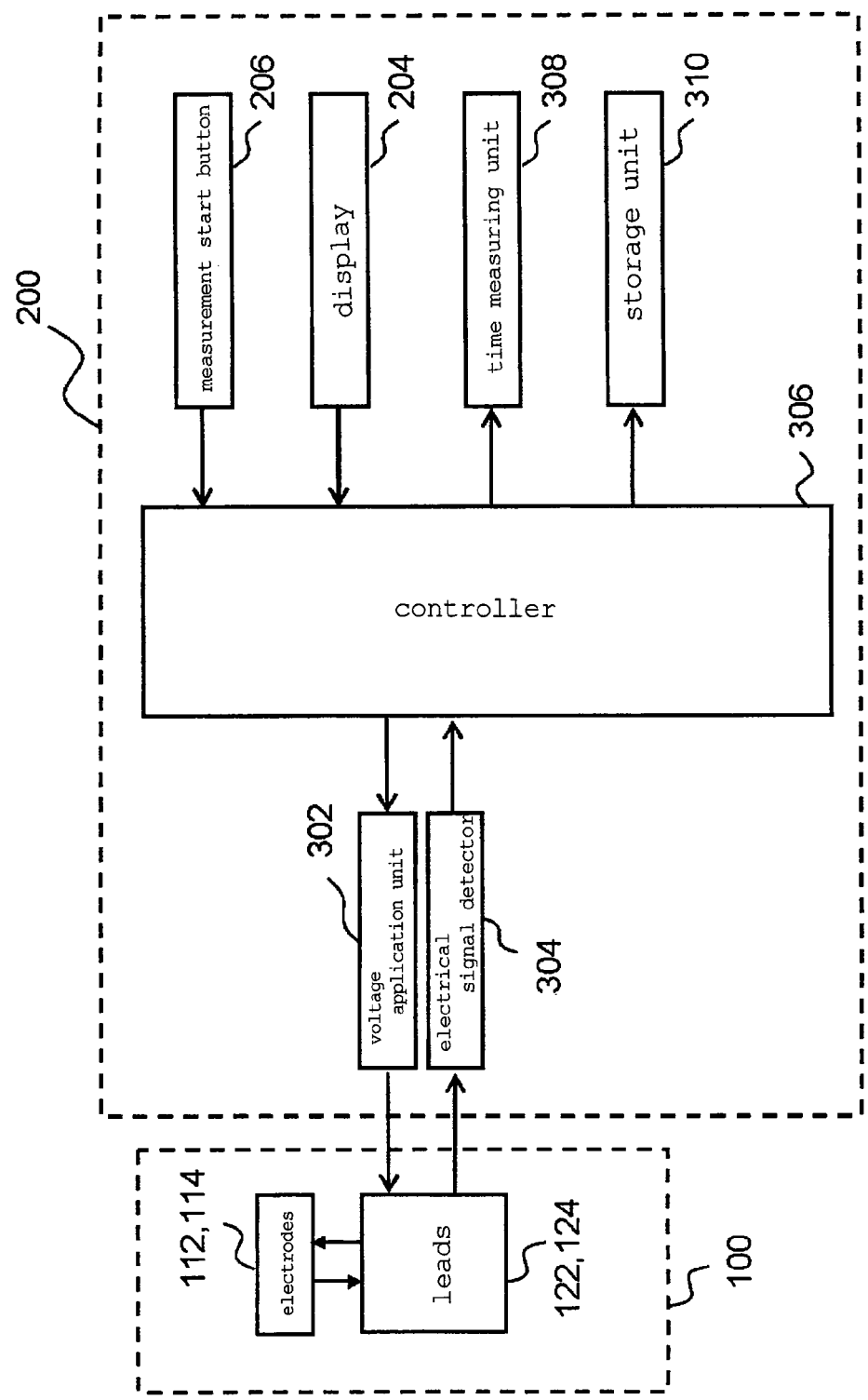
FIG. 3 is a block diagram showing the configuration of the apparatus for measuring creatinine concentration in the same embodiment.

Next, an apparatus 200 for measuring creatinine concentration according to this embodiment and the method for measuring creatinine concentration using this apparatus are described with reference to FIGS. 2 and 3. FIG. 2 is a perspective view showing the appearance of the measuring apparatus 200, and FIG. 3 is a block diagram showing the configuration of the measuring apparatus 200.

First, the structure of the measuring apparatus 200 is described with reference to FIG. 2.

A housing 202 of the measuring apparatus 200 has a measuring device mounting port 208 for mounting the measuring device 100, a display 204 for displaying measurement results etc., and a measurement start button 206 for starting the measurement of creatinine concentration by the measuring apparatus 200. Inside the measuring device mounting port 208 are a first terminal and a second terminal, which are to be electrically connected to the first lead 122 and the second lead 124 of the measuring device 100, respectively.

Next, the configuration inside the housing 202 of the measuring apparatus 200 is described with reference to FIG. 3.

The housing 202 of the measuring apparatus 200 contains a voltage application unit 302, an electrical signal detector 304, a controller 306, a time measuring unit 308, and a storage unit 310.

The voltage application unit 302 has the function of applying a voltage or potential to the first electrode 112 and the second electrode 114 of the measuring device 100 mounted in the measuring device mounting port 208. The voltage or potential is applied through the first terminal and the second terminal electrically connected to the first lead 122 and the second lead 124 of the measuring device 100, respectively.

The electrical signal detector 304 has the function of detecting the electrical signal from the first electrode 112 and the second electrode 114 through the first terminal and the second terminal. The electrical signal detector 304 corresponds to the detector of the invention.

The storage unit 310 stores correlation data corresponding to a calibration curve which indicates a correlation between creatinine concentrations and electrical signals detected by the electrical signal detector 304. Examples of the storage unit 310 include memory such as RAM and ROM.

The controller 306 has the function of converting the electrical signal detected by the electrical signal detector 304 to creatinine concentration by referring to the correlation data. The controller 306 corresponds to the arithmetic unit of the invention. Examples of the controller 306 include microcomputers such as a CPU (Central Processing Unit).

Next, the method for measuring creatinine concentration using the measuring device 100 and the measuring apparatus 200 according to this embodiment is described.

First, a user inserts the lead side of the measuring device 100 into the measuring device mounting port 208 of the measuring apparatus 200. As a result, the first lead 122 and the second lead 124 of the measuring device 100 come into contact with and are electrically connected to the first terminal and the second terminal inside the measuring device mounting port 208, respectively.

When the measuring device 100 is inserted into the measuring device mounting port 208, an insertion detecting switch is turned on, so that a signal is sent to the controller 306. The insertion detecting switch comprises a microswitch installed in the measuring device mounting port 208. When the controller 306 detects the insertion of the measuring device 100 from the signal sent from the insertion detecting switch, the controller 306 controls the voltage application unit 302, so that a voltage (e.g., 0.2 V) is applied between the first electrode 112 and the second electrode 114 through the first terminal and the second terminal in order to detect the introduction of a sample.

Next, the user brings a sample into contact with the sample inlet 132 of the measuring device 100. Upon the contact, the sample (e.g., approximately 0.6 µL) is sucked into the sample holding space of the measuring device 100 from the sample inlet 132 by capillarity, so that the sample holding space is filled with the sample. When the sample comes into contact with the first electrode 112 and the second electrode 114, a current flows between the first electrode 112 and the second electrode 114 through the sample. The resultant change in electrical signal is detected by the electrical signal detector 304.

When the controller 306 detects the introduction of the sample into the sample holding space from the signal sent from the electrical signal detector 304, the controller 306 controls the voltage application unit 302, so that the voltage applied by the voltage application unit 302 is changed to a different voltage (e.g., 0 V or open circuit). Also, upon the detection of introduction of the sample, the controller 306 causes the time measuring unit 308, which is a timer, to start measuring time.

When the sample comes into contact with the reagent layer 130 exposed in the sample holding space, M-PMS contained in the reagent layer 130 dissolves in the sample. The dissolved M-PMS in the sample directly reacts with creatinine contained in the sample, thereby forming reaction products (an oxidation product of creatinine and reduced M-PMS).

When the controller 306 determines from the signal sent from the time measuring unit 308 that a predetermined time (e.g., 60 seconds) has passed, the controller 306 controls the voltage application unit 302, so that a voltage is applied between the first electrode 112 and the second electrode 114 in order to measure the concentration of the reduced M-PMS. For example, a voltage is applied so as to make the first electrode 112 +0.6 V relative to the second electrode 114. After a certain time (e.g., five seconds) from the voltage application, an electrical signal such as the current flowing between the first electrode 112 and the second electrode 114 is measured by the electrical signal detector 304. At this time, the reduced M-PMS is oxidized at the first electrode 112. Therefore, the electrical signal measured by the electrical signal detector 304 is dependent on the creatinine concentration in the sample.

The controller 306 reads the correlation data which indicates a correlation between electrical signals and creatinine concentrations stored in the storage unit 310 and refers to it. As a result, the electrical signal detected by the electrical signal detector 304 is converted to the creatinine concentration in the sample.

The creatinine concentration thus determined is displayed on the display 204. Upon the display of the creatinine concentration on the display 204, the user may recognize that the measurement of the creatinine concentration has been completed. It is preferred to store the creatinine concentration thus obtained in the storage unit 310 together with the time measured by the time measuring unit 308.

According to the measuring device 100, unlike conventional measuring devices, creatinine directly reacts with M-PMS in the sample holding space in the absence of picric acid and any enzyme responsive to creatinine. Therefore, the reaction proceeds without being affected by interferents including ion species such as salt, urea, amino acids, sugars, and acetone. Hence, even in the case of using a biological sample such as urine or blood, it is possible to quantify creatinine contained in the sample with a better accuracy than that of conventional measuring devices. Also, due to the presence of the monovalent anion in the sample, M-PMS becomes stable in the presence of the phosphate buffers. Hence, when a monovalent anion is present in a sample, it is possible to quantify creatinine contained in the sample with better reproducibility.

In this embodiment, it is preferable to use sodium methyl sulfate as an electrolyte salt of a monovalent anion, but the use of an electrolyte salt of a monovalent anion is not indispensable. Also, the electrolyte salt of a monovalent anion is not to be construed as being limited to sodium methyl sulfate. Instead of sodium methyl sulfate, it is also possible to use lithium chloride, sodium chloride, potassium chloride, lithium nitrate, sodium nitrate, potassium nitrate, lithium methyl sulfate, sodium methyl sulfate, potassium methyl sulfate, and the like. Even in the case of using such an electrolyte salt of a monovalent anion, due to the presence of the monovalent anion in a sample, M-PMS becomes stable in the presence of a phosphate buffer.

This embodiment has shown an example in which the measuring device has one reagent layer, but this is not to be construed as limiting. The measuring device may have two reagent layers, for example, a first reagent layer containing a creatinine quantitative reagent and a second reagent layer containing a phosphate buffer.

This embodiment has shown an example in which when the controller detects the introduction of a sample into the sample holding space, the voltage applied by the voltage application unit is changed to a different voltage, but this is not to be construed as limiting. The voltage applied by the voltage application unit does not always need to be changed as long as a current dependent on the creatinine concentration is obtained. It is also possible to apply a voltage necessary for a measurement (e.g., such a voltage that the first electrode is +0.6 V relative to the second electrode) from the detection of insertion of the measuring device and continue to apply that voltage after the detection of introduction of a sample.

This embodiment has shown an example in which the potential applied to the first electrode to obtain the electrical signal corresponding to the reduced M-PMS concentration is 0.6 V relative to the second electrode, but this is not to be construed as limiting. The voltage between the first electrode and the second electrode may be any voltage at which M-PMS reduced in the redox reaction between creatinine and M-PMS is oxidized.

This embodiment has shown an example in which the time (reaction time) from the detection of introduction of a sample to the detection of an electrical signal is 60 seconds, but the time does not always need to be that value. The reaction time may be shorter than the above-mentioned value if the difference in current value corresponding to the difference in creatinine concentration may be effectively detected. If the reaction time is made longer, the reaction between creatinine and M-PMS is more likely to reach a complete or steady state. Hence, the amount of creatinine may be quantified more accurately without being affected by ambient conditions such as temperature.

This embodiment has shown an example in which an electrical signal is detected five seconds after the application of a potential to the electrodes, but this time is not to be construed as limiting. This time may be any time when the difference in electrical signal corresponding to the difference in creatinine concentration may be effectively detected.

Also, the shape, number, layout, etc. of the electrode system, leads, and terminals are not to be construed as being limited to those of this embodiment. This also applies to the other embodiments.

In order to facilitate the introduction of a sample into the sample holding space of the measuring device, a lecithin layer may be formed by dissolving lecithin in toluene or another organic solvent to prepare a solution, applying the solution onto the inner wall of the second substrate, and drying it. With this structure, the sample amount may be made constant with better reproducibility. It is thus possible to quantify creatinine contained in a sample with better accuracy.

The apparatus for measuring creatinine concentration may further include a recorder for recording measurement results in a storage medium such as an SD card. When measurement results are stored in a removable storage medium, the measurement results may be readily taken out of the measuring apparatus. It is thus easy to have the measurement results analyzed by an analytical laboratory.

The measuring apparatus may further include a transmitter for transmitting measurement results to outside of the measuring apparatus. In this case, the measurement results may be transmitted to an analytical department in a hospital, an analytical laboratory, or the like. Hence, the time from the measurement to the analysis by the analytical department, analytical laboratory, or the like may be shortened.

The measuring apparatus may further include a receiver for receiving the results of analysis by an analytical department, an analytical laboratory, or the like. This permits prompt feedback of the analysis results to the user.

Embodiment 2

Figure 4:
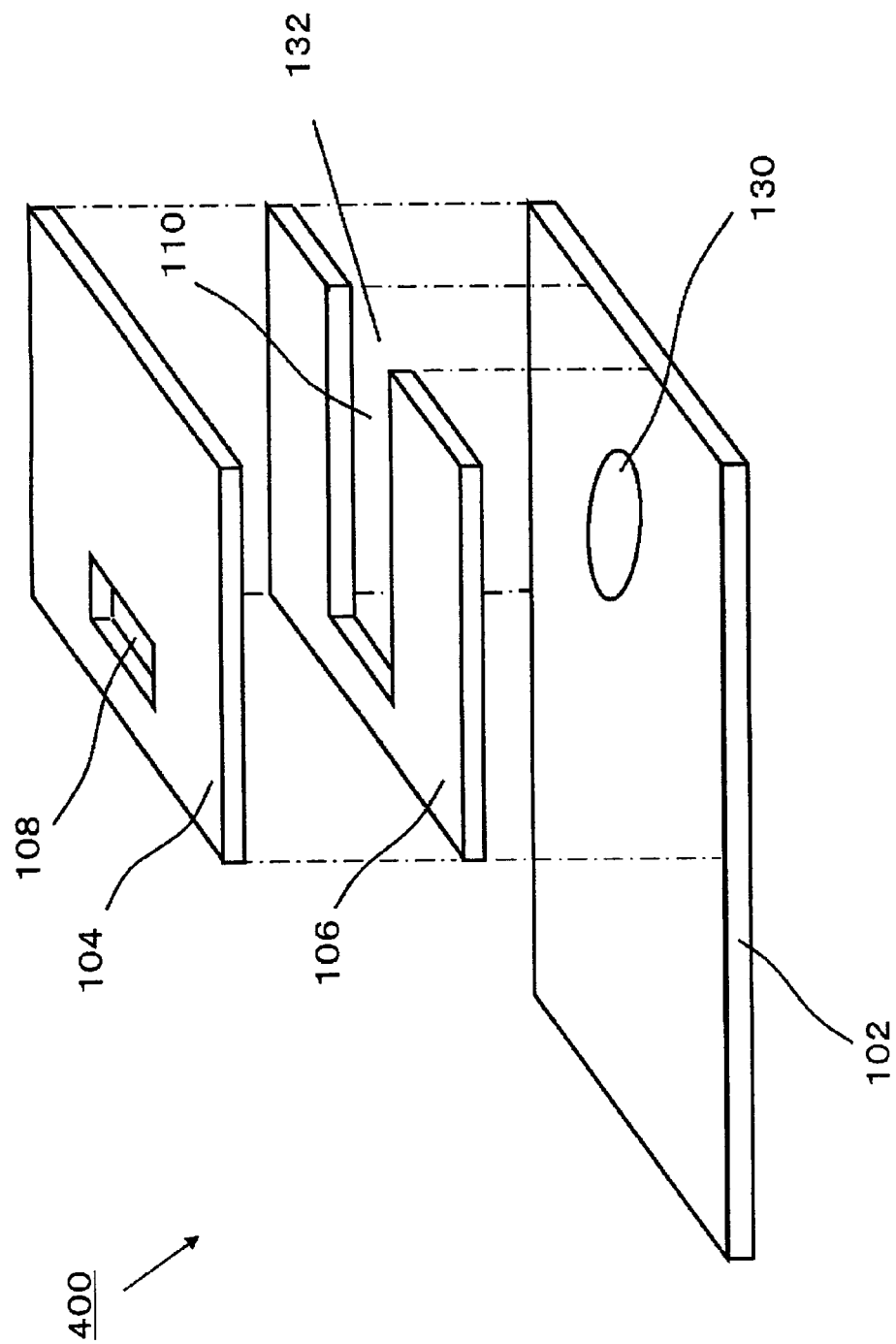
FIG. 4 is an exploded perspective view showing the structure of a device for measuring creatinine concentration in Embodiment 2 of the invention.

Next, a device 400 for measuring creatinine concentration according to Embodiment 2 of the invention is described with reference to FIG. 4. FIG. 4 is an exploded perspective view showing the structure of the measuring device 400.

The measuring device 400 is used in a method for optically quantifying the concentration of creatinine contained in a sample. The measuring device 400 is composed of a first substrate 102 and a second substrate 104 with an air vent 108 which are combined so as to sandwich a spacer 106 with a slit 110. The first substrate 102, the second substrate 104, and the spacer 106 are made of, for example, polyethylene terephthalate.

In the measuring device 400, unlike the measuring device 100 according to Embodiment 1, the first substrate 102 does not have a first electrode 112, a second electrode 114, a first lead 122, and a second lead 124. Also, a reagent layer 130, which is the same as that of Embodiment 1, is disposed on the first substrate 102, not on the first electrode 112 and the second electrode 114. The dimensions of the first substrate 102 may be suitably set; for example, the width is approximately 7 mm, the length is approximately 30 mm, and the thickness is approximately 0.7 mm.

Next, the method for producing the measuring device 400 is described.

First, a given amount of an aqueous solution containing a creatinine quantitative reagent, which is the same as that of Embodiment 1, is dropped on the first substrate 102 by using a microsyringe or the like. Thereafter, the first substrate 102 is left for drying in an environment at room temperature to approximately 30° C., to form the reagent layer 130. The concentration and amount of the reagent containing aqueous solution to be applied thereto may be selected depending on the characteristics and size of the necessary device; for example, they may be selected in the same manner as in Embodiment 1.

Next, the first substrate 102 with the reagent layer 130 formed thereon is combined with the spacer 106 and the second substrate 104. Adhesive is applied to the portions of the first substrate 102, the spacer 106, and the second substrate 104 to be bonded. They are laminated, pressed, and allowed to stand for bonding. Instead of this method, it is also possible to combine them without applying adhesive and then thermally or ultrasonically bond the bonding portions by using a commercially available welding machine.

When the first substrate 102, the spacer 106, and the second substrate 104 are combined, a space is formed by the slit 110 of the spacer 106 between the first substrate 102 and the second substrate 104, and this space serves as a sample holding space. Also, the opening of the slit 110 serves as a sample inlet 132.

Figure 5:
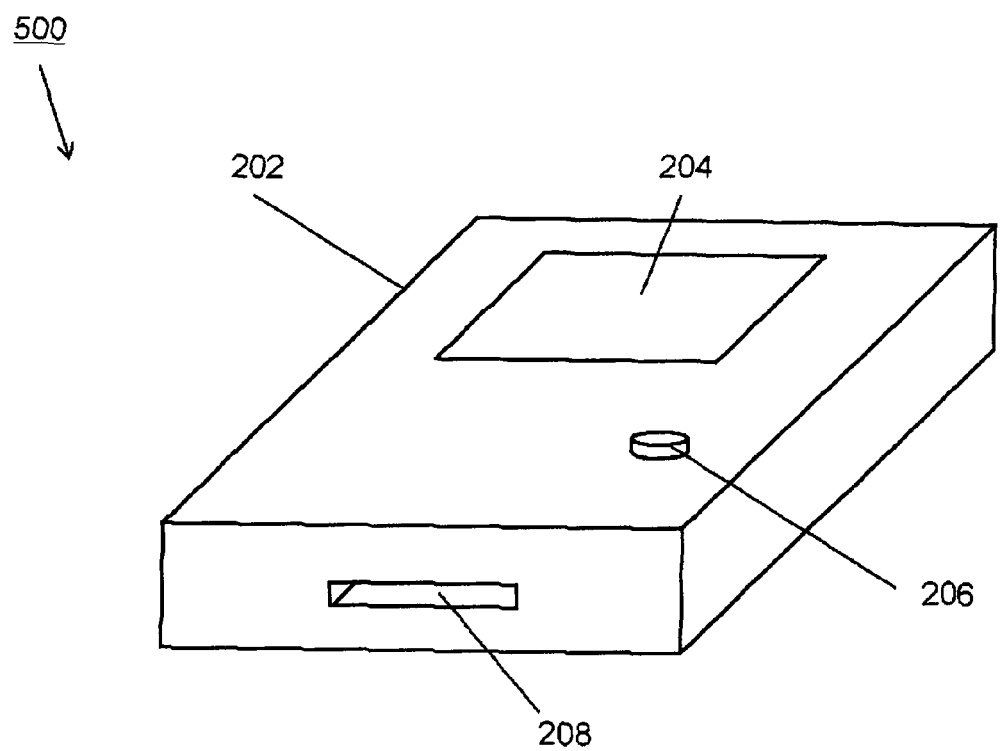
FIG. 5 is a perspective view showing the appearance of an apparatus for measuring creatinine concentration in the same embodiment.
Figure 6:
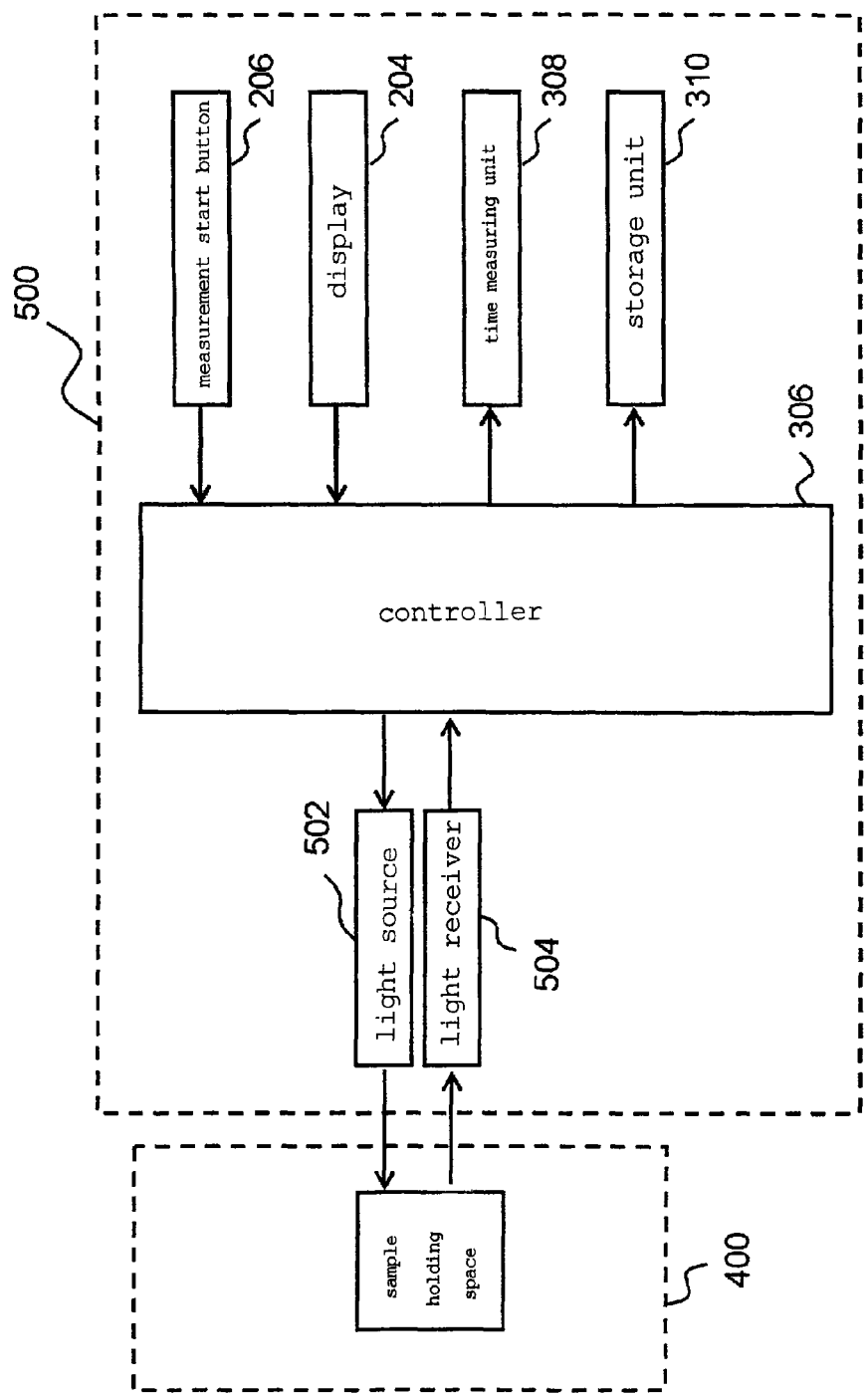
FIG. 6 is a block diagram showing the configuration of the apparatus for measuring creatinine concentration in the same embodiment.

Next, an apparatus 500 for measuring creatinine concentration according to this embodiment and the method for measuring creatinine concentration using this apparatus are described with reference to FIGS. 5 and 6. FIG. 5 is a perspective view showing the appearance of the measuring apparatus 500, and FIG. 6 is a block diagram showing the configuration of the measuring apparatus 500.

First, the structure of the measuring apparatus 500 is described with reference to FIG. 5.

A housing 202 of the measuring apparatus 500 has a measuring device mounting port 208 for mounting the measuring device 400, a display 204 for displaying measurement results etc., and a measurement start button 206 for starting the measurement of creatinine concentration by the measuring apparatus 500.

Next, the configuration inside the housing 202 of the measuring apparatus 500 is described with reference to FIG. 6.

The housing 202 of the measuring apparatus 500 contains a light source 502, a light receiver 504, a controller 306, a time measuring unit 308, and a storage unit 310.

The light source 502 has the function of emitting light to the sample holding space of the measuring device 400 mounted in the measuring device mounting port 208. The wavelength of the light emitted from the light source 502 may be selected such that the absorption intensity changes depending on the reaction between M-PMS and creatinine. An example of the light source 502 is a blue green LED which emits light with the wavelength range including 510 nm.

The light receiver 504 has the function of detecting the light emitted from the light source 502 and reflected from the sample holding space of the measuring device 400 mounted in the measuring device mounting port 208.

The storage unit 310 stores correlation data corresponding to a calibration curve which indicates a correlation between creatinine concentrations and reflected light intensities detected by the light receiver 504. Examples of the storage unit 310 include memory such as RAM and ROM.

The controller 306 has the function of converting the intensity of the reflected light detected by the light receiver 504 to creatinine concentration by referring to the correlation data. The controller 306 corresponds to the arithmetic unit of the invention. Examples of the controller 306 include microcomputers such as a CPU (Central Processing Unit).

Next, the method for measuring creatinine concentration using the measuring device 400 and the measuring apparatus 500 according to this embodiment is described.

First, a user inserts the other side of the measuring device 400 from the sample inlet 132 into the measuring device mounting port 208 of the measuring apparatus 500.

When the measuring device 400 is inserted into the measuring device mounting port 208, an insertion detecting switch is turned on, so that a signal is sent to the controller 306. The insertion detecting switch comprises a microswitch installed in the measuring device mounting port 208. When the controller 306 detects the insertion of the measuring device 400 from the signal sent from the insertion detecting switch, the controller 306 actuates the light source 502. As a result, light is emitted to the sample holding space of the measuring device 400 from the light source 502.

Next, the user brings a sample into contact with the sample inlet 132 of the measuring device 400. Upon the contact, the sample is sucked into the sample holding space of the measuring device 400 from the sample inlet 132 by capillarity, so that the sample holding space is filled with the sample. When the sample reaches the position of the sample holding space to which the light is emitted, the transmittance inside the sample holding space changes. The resulting change in the intensity of reflected light is detected by the light receiver 504.

When the controller 306 detects the introduction of the sample into the sample holding space from the signal sent from the light receiver 504, the controller 306 causes the time measuring unit 308, which is a timer, to start measuring time.

When the sample comes into contact with the reagent layer 130 exposed in the sample holding space, M-PMS contained in the reagent layer 130 dissolves in the sample. The dissolved M-PMS in the sample directly reacts with creatinine contained in the sample, thereby forming reaction products (an oxidation product of creatinine and reduced M-PMS). The decrease of the M-PMS due to reduction causes a change in the absorption spectrum of the sample. The amount of the change in the absorption spectrum of the sample is dependent on the concentration of the reduced M-PMS.

When the controller 306 determines from the signal sent from the time measuring unit 308 that a predetermined time (e.g., 60 seconds) has passed, it causes the light receiver 504 to measure the intensity of the light reflected from the sample holding space. The intensity of the reflected light measured by the light receiver 504 is dependent on the concentration of creatinine contained in the sample.

The controller 306 reads the correlation data corresponding to a calibration curve which is stored in the storage unit 310 and which indicates a correlation between creatinine concentrations and reflected light intensities detected by the light receiver 504, and refers to it. As a result, the intensity of the reflected light detected by the light receiver 504 is converted to the creatinine concentration in the sample.

The creatinine concentration thus determined is displayed on the display 204. Upon the display of the creatinine concentration on the display 204, the user may recognize that the measurement has been completed. It is preferred to store the creatinine concentration thus obtained in the storage unit 310 together with the time measured by the time measuring unit 308.

According to the measuring device 400, unlike conventional measuring devices, creatinine directly reacts with M-PMS in the sample holding space in the absence of picric acid and any enzyme responsive to creatinine. Therefore, the reaction proceeds without being affected by interferents including ion species such as salt, urea, amino acids, sugars, and acetone. Therefore, even in the case of using a biological sample such as urine or blood, it is possible to quantify creatinine contained in the sample with better accuracy and reproducibility than that of conventional measuring devices. Also, in the same manner as in Embodiment 1, when a monovalent anion is present in a sample, it is possible to quantify creatinine contained in the sample with better reproducibility. In this embodiment, also, the electrolyte salt of a monovalent anion is not to be construed as being limited to sodium methyl sulfate.

In this embodiment, the measuring device may include two or more reagent layers in the same manner as in Embodiment 1.

This embodiment has shown an example in which the time (reaction time) from the detection of introduction of a sample to the detection of reflected light intensity is 60 seconds, but the time does not always need to be that value. The reaction time may be shorter than the above-mentioned value if the difference in reflected light intensity corresponding to the difference in creatinine concentration is effectively detected. If the reaction time is made longer, the amount of creatinine may be quantified more accurately in the same manner as in Embodiment 1.

In order to facilitate the introduction of a sample into the sample holding space, the measuring device may have a lecithin layer in the same manner as in Embodiment 1.

In the same manner as in Embodiment 1, the apparatus for measuring creatinine concentration may further include a recorder for recording measurement results in a storage medium such as an SD card. Also, the measuring apparatus may further include a transmitter for transmitting measurement results to outside of the measuring apparatus. Further, the measuring apparatus may further include a receiver for receiving the results of analysis by an analytical department, an analytical laboratory, or the like.

Embodiment 3

Figure 7:
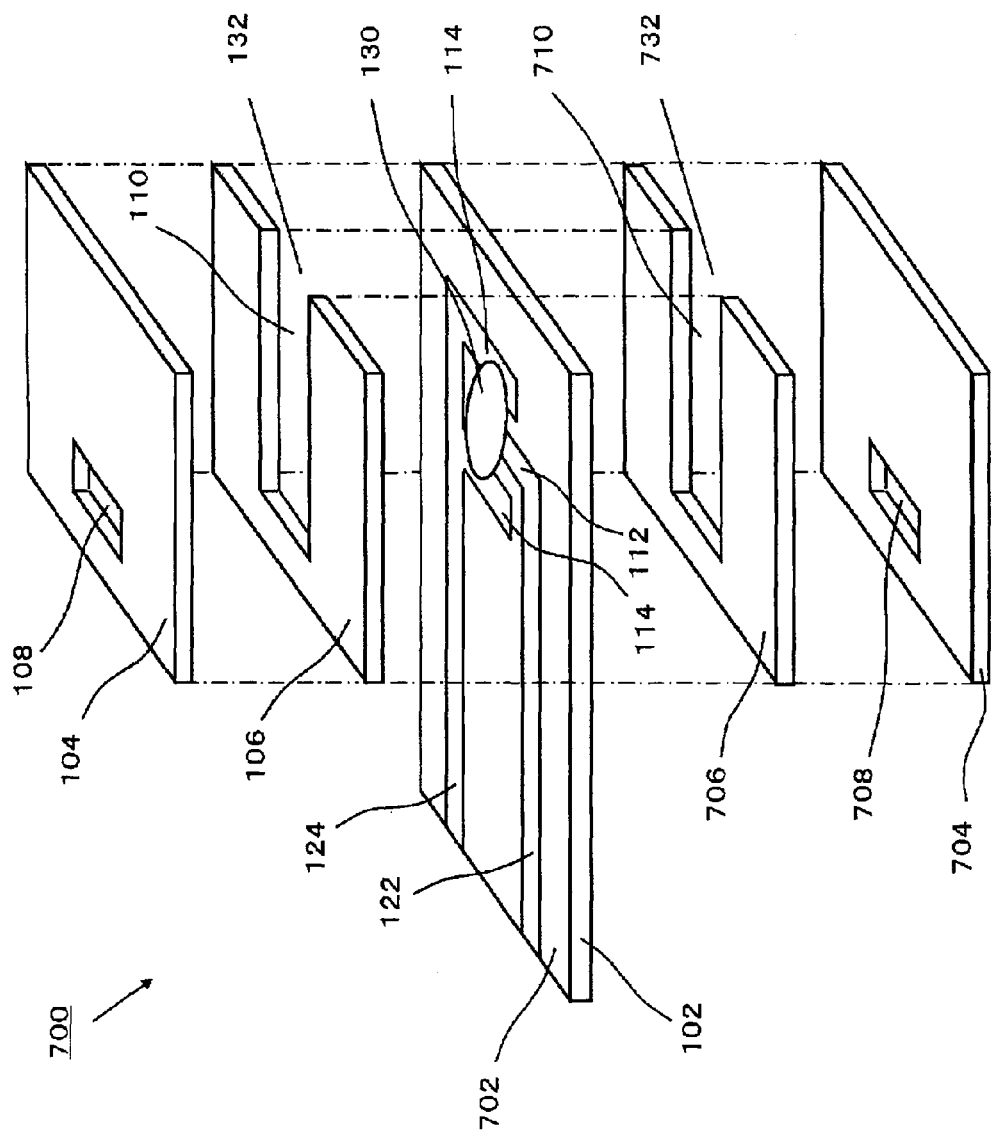
FIG. 7 is an exploded perspective view showing the structure of a device for measuring the amount of salt in Embodiment 3 of the invention seen from the first face side of the first substrate.
Figure 8:
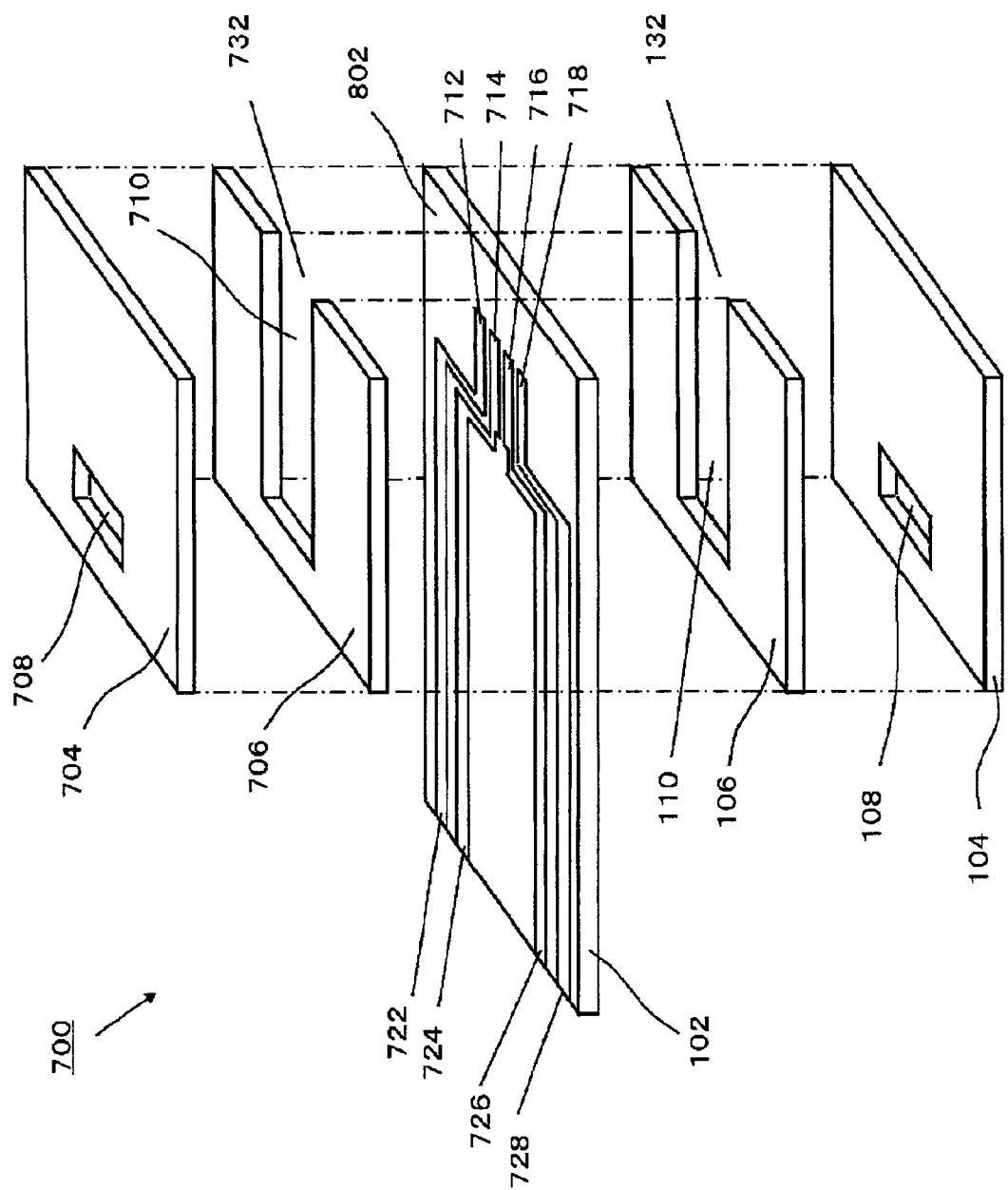
FIG. 8 is an exploded perspective view showing the structure of the device for measuring the amount of salt seen from the second face side of the first substrate in the same embodiment.

Next, a device 700 for measuring the amount of salt according to Embodiment 3 of the invention is described with reference to FIGS. 7 and 8. FIG. 7 is an exploded perspective view showing the structure of the measuring device 700 seen from the first face side of the first substrate, and FIG. 8 is an exploded perspective view showing the structure seen from the second face side of the first substrate.

The measuring device 700 is used in a method of electrochemically measuring creatinine contained in urine (sample) and measuring an electrical property of the urine in order to estimate the amount of urinary salt excretion in a day from the results of these measurements.

In the measuring device 700, a first face 702 of an insulating first substrate 102 is in contact with an insulating first spacer 106 with a slit 110, and the first substrate 102 is combined with an insulating second substrate 104 with an air vent 108 so as to sandwich the first spacer 106. Further, a second face 802 of the first substrate 102 is in contact with an insulating second spacer 706 with a slit 710, and the first substrate 102 is combined with an insulating third substrate 704 with an air vent 708 so as to sandwich the second spacer 706. The first substrate 102, the first spacer 106, the second substrate 104, the second spacer 706, and the third substrate 704 are made of, for example, polyethylene terephthalate.

The first substrate 102 has, on the first face 702, a first electrode 112, a second electrode 114, a first lead 122 electrically connected to the first electrode 112, and a second lead 124 electrically connected to the second electrode 114, as in the measuring device 100 of Embodiment 1. Disposed on the first electrode 112 and the second electrode 114 is a reagent layer 130 containing a creatinine quantitative reagent.

Disposed on the second face 802 of the first substrate 102 are a third electrode 712, a fourth-electrode 714, a fifth electrode 716, and a sixth electrode 718. Further disposed on the second face 802 are a third lead 722 electrically connected to the third electrode 712, a fourth lead 724 electrically connected to the fourth electrode 714, a fifth lead 726 electrically connected to the fifth electrode 716, and a sixth lead 728 electrically connected to the sixth electrode 718. The dimensions of the first substrate 102 may be suitably set; for example, the width is approximately 7 mm, the length is approximately 30 mm, and the thickness is approximately 0.7 mm.

Next, the method for producing the measuring device 700 is described.

First, palladium is sputtered onto the first face 702 of the first substrate 102 with a resin mask of an electrode pattern thereon, to form the first electrode 112, the second electrode 114, the first lead 122, and the second lead 124. The first electrode 112 and the second electrode 114 are electrically connected to the terminals of an apparatus for measuring the amount of salt, which will be described below, by the first lead 122 and the second lead 124, respectively.

Next, palladium is sputtered onto the second face 802 of the first substrate 102 with a mask of a different electrode pattern from that of the above-mentioned mask, to form the third electrode 712, the fourth electrode 714, the fifth electrode 716, the sixth electrode 718, the third lead 722, the fourth lead 724, the fifth lead 726, and the sixth lead 728. The third electrode 712, the fourth electrode 714, the fifth electrode 716, and the sixth electrode 718 are electrically connected to the terminals of the apparatus for measuring the amount of salt, described below, by the third lead 722, the fourth lead 724, the fifth lead 726, and the sixth lead 728, respectively.

Next, a given amount of an aqueous solution containing a creatinine quantitative reagent, which is the same as that of Embodiment 1, is dropped on the first electrode 112 and the second electrode 114 formed on the first face 702 of the first substrate 102 by using a microsyringe or the like. Thereafter, the first substrate 102 is left for drying in an environment at room temperature to approximately 30° C., to form the reagent layer 130. The concentration and amount of the reagent containing aqueous solution to be applied thereto may be selected depending on the characteristics and size of the necessary device; for example, they may be selected in the same manner as in Embodiment 1.

Subsequently, the second substrate 104, the first spacer 106, the first substrate 102, the second spacer 706, and the third substrate 704 are combined so that the first face 702 of the first substrate 102 contacts the first spacer 106 and the second face 802 of the first substrate 102 contacts the second spacer 706. Adhesive is applied to the portions of the respective components to be bonded, and they are laminated, pressed, and allowed to stand for bonding. Instead of this method, it is also possible to combine them without applying adhesive and then thermally or ultrasonically bond the bonding portions by using a commercially available welding machine.

When the first substrate 102, the first spacer 106, and the second substrate 104 are combined, a space is formed by the slit 110 of the first spacer 106 between the first substrate 102 and the second substrate 104, and this space serves as a first sample holding space for measuring creatinine concentration. Also, the opening of the slit 110 serves as a first sample inlet 132 for measuring creatinine concentration.

When the first substrate 102, the second spacer 706, and the third substrate 704 are combined, a space is formed by the slit 710 of the second spacer 706 between the first substrate 102 and the third substrate 704, and this space serves as a second sample holding space for measuring an electrical property of urine. Also, the opening of the slit 710 serves as a second sample inlet 732 for measuring an electrical property of urine.

Figure 10:
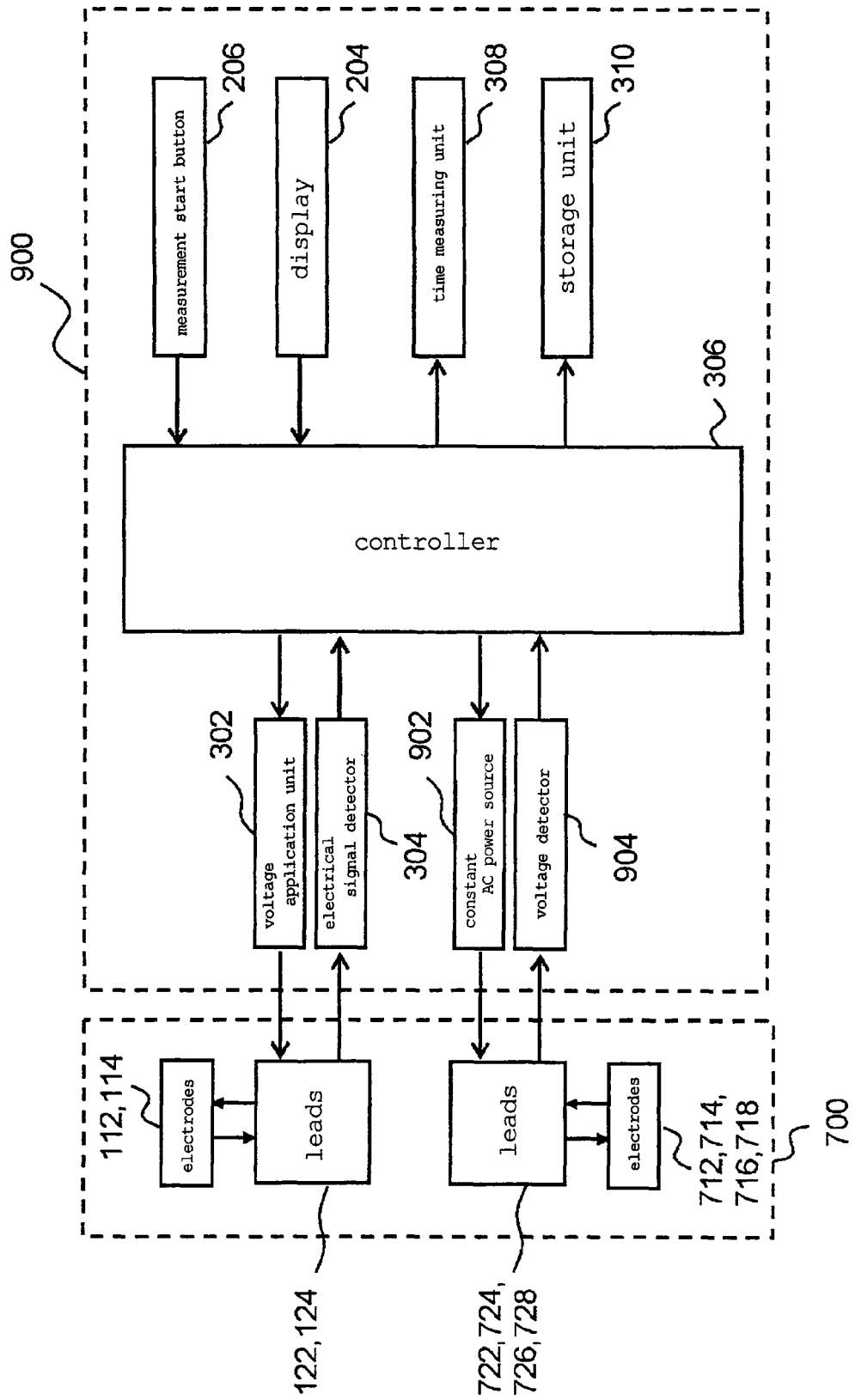
FIG. 10 is a block diagram showing the configuration of the apparatus for measuring the amount of salt in the same embodiment.

Next, an apparatus 900 for measuring the amount of salt according to this embodiment and the method for measuring the amount of salt using this apparatus are described with reference to FIGS. 9 and 10. FIG. 9 is a perspective view showing the appearance of the measuring apparatus 900, and FIG. 10 is a block diagram showing the configuration of the measuring apparatus 900.

First, the structure of the measuring apparatus 900 is described with reference to FIG. 9.

A housing 202 of the measuring apparatus 900 has a measuring device mounting port 208 for mounting the measuring device 700, a display 204 for displaying measurement results etc., and a measurement start button 206 for starting the measurement of creatinine concentration and an electrical property of urine by the measuring apparatus 900. Inside the measuring device mounting port 208 are a first terminal, a second terminal, a third terminal, a fourth terminal, a fifth terminal, and a sixth terminal, which are to be electrically connected to the first lead 122, the second lead 124, the third lead 722, the fourth lead 724, the fifth lead 726, and the sixth lead 728 of the measuring device 700, respectively.

Next, the configuration inside the housing 202 of the measuring apparatus 900 is described with reference to FIG. 10.

The housing 202 of the measuring apparatus 900 contains a voltage application unit 302, an electrical signal detector 304, a constant AC power source 902, a voltage detector 904, a controller 306, a time measuring unit 308, and a storage unit 310.

The voltage application unit 302 has the function of applying a voltage or potential to the first electrode 112 and the second electrode 114 of the measuring device 700 mounted in the measuring device mounting port 208. The voltage or potential is applied through the first terminal and the second terminal electrically connected to the first lead 122 and the second lead 124 of the measuring device 700, respectively.

The electrical signal detector 304 has the function of detecting the electrical signal from the first electrode 112 and the second electrode 114 through the first terminal and the second terminal. The electrical signal detector 304 corresponds to the detector of the invention.

The constant AC power source 902 has the function of applying a constant alternating current between the third electrode 712 and the sixth electrode 718 of the measuring device 700 mounted in the measuring device mounting port 208. The constant alternating current is applied through the third terminal and the sixth terminal electrically connected to the third lead 722 and the sixth lead 728 of the measuring device 700, respectively. The alternating current applied has, for example, a frequency of approximately 1 kHz and a current value of approximately 0.1 mA.

The voltage detector 904 has the function of detecting the voltage (effective value of alternating voltage) between the fourth electrode 714 and the fifth electrode 716 through the fourth terminal and the fifth terminal.

The storage unit 310 stores:

(i) first correlation data corresponding to a first calibration curve which indicates a correlation between creatinine concentrations and electrical signals detected by the electrical signal detector 304;

(ii) second correlation data corresponding to a second calibration curve which indicates a correlation between salt concentrations and voltages detected by the voltage detector 904; and (iii) third correlation data corresponding to a third calibration curve which indicates a correlation between the amounts of urinary salt excretion per day and salt concentrations corrected by creatinine concentration.

Examples of the storage unit 310 include memory such as RAM and ROM.

The controller 306 has the functions of:

(I) converting the electrical signal detected by the electrical signal detector 304 to creatinine concentration by referring to the first correlation data;

(II) converting the voltage detected by the voltage detector 904 to salt concentration by referring to the second correlation data;

(III) correcting the salt concentration by using the creatinine concentration thus obtained; and (IV) converting the corrected salt concentration to the amount of urinary salt excretion per day by referring to the third correlation data.

The controller 306 corresponds to the arithmetic unit of the invention. Examples of the controller 306 include microcomputers such as a CPU (Central Processing Unit).

Next, the method for measuring the amount of urinary salt using the measuring device 700 and the measuring apparatus 900 according to this embodiment is described.

First, a user inserts the lead side of the measuring device 700 into the measuring device mounting port 208 of the measuring apparatus 900. As a result, the first lead 122, the second lead 124, the third lead 722, the fourth lead 724, the fifth lead 726, and the sixth lead 728 of the measuring device 700 are electrically connected to the first terminal, the second terminal, the third terminal, the fourth terminal, the fifth terminal, and the sixth terminal inside the measuring device mounting port 208, respectively.

When the measuring device 700 is inserted into the measuring device mounting port 208, an insertion detecting switch is turned on, so that a signal is sent to the controller 306. The insertion detecting switch comprises a microswitch installed in the measuring device mounting port 208. When the controller 306 detects the insertion of the measuring device 700 from the signal sent from the insertion detecting switch, the controller 306 controls the voltage application unit 302, so that a voltage (e.g., 0.2 V) is applied between the first electrode 112 and the second electrode 114 through the first terminal and the second terminal.

Subsequently, the user brings a sample into contact with the first sample inlet 132 and the second sample inlet 732 of the measuring device 700. Due to this contact, the sample is sucked into the two sample holding spaces of the measuring device 700 from the first sample inlet 132 and the second sample inlet 732 by capillarity, so that the two sample holding spaces are filled with the sample.

When the sample comes into contact with the first electrode 112 and the second electrode 114 in the first sample holding space, a current flows between the first electrode 112 and the second electrode 114 through the sample. The resulting change in electrical signal is detected by the electrical signal detector 304.

From the signal sent from the electrical signal detector 304, the controller 306 detects the introduction of the sample into the first and second sample holding spaces.

When the controller 306 detects the introduction of the sample into the first and second sample holding spaces, the controller 306 controls the voltage application unit 302, so that the voltage applied by the voltage application unit 302 is changed to a different voltage (e.g., 0 V or open circuit). Also, upon the detection of introduction of the sample, the controller 306 causes the time measuring unit 308, which is a timer, to start measuring time.

Upon the detection of introduction of the sample into the second sample holding space, the controller 306 controls the constant AC power source 902, so that a constant alternating current (e.g., frequency 1 kHz, current value 0.1 mA) is applied between the third electrode 712 and the sixth electrode 718 through the third terminal and the sixth terminal. After a predetermined time (e.g., after five seconds) from the application of the alternating current, the voltage detector 904 measures the voltage (effective value of alternating voltage) between the fourth electrode 714 and the fifth electrode 716.

The controller 306 reads the second correlation data which is stored in the storage unit 310 and which indicates a correlation between salt concentrations and voltages detected by the voltage detector 904, and refers to it. As a result, the voltage detected by the voltage detector 904 is converted to the salt concentration in the sample. The salt concentration thus determined is displayed on the display 204.

When the sample comes into contact with the reagent layer 130 in the first sample holding space, M-PMS contained in the reagent layer 130 dissolves in the sample. The dissolved M-PMS in the sample directly reacts with creatinine contained in the sample, thereby forming reaction products (an oxidation product of creatinine and reduced M-PMS).

When the controller 306 determines from the signal sent from the time measuring unit 308 that a predetermined time (e.g., 60 seconds) has passed, the controller 306 controls the voltage application unit 302, so that a different voltage is applied again between the first electrode 112 and the second electrode 114 (for example, such a voltage that the first electrode 112 is +0.6 V relative to the second electrode 114). After a certain time (e.g., five seconds) from the voltage application, an electrical signal such as the current flowing between the first electrode 112 and the second electrode 114 is measured by the electrical signal detector 304. At this time, the reduced M-PMS is oxidized at the first electrode 112. The electrical signal measured by the electrical signal detector 304 is dependent on the creatinine concentration in the sample.

The controller 306 reads the first correlation data which is stored in the storage unit 310 and which indicates a correlation between electrical signals and creatinine concentrations, and refers to it. As a result, the electrical signal detected by the electrical signal detector 304 is converted to the creatinine concentration in the sample.

Thereafter, the controller 306 corrects the salt concentration by using the creatinine concentration thus obtained. The controller 306 then reads the third correlation data which is stored in the storage unit 310 and which corresponds to the third calibration curve indicating a correlation between the amounts of urinary salt excretion per day and salt concentrations corrected by creatinine concentration, and refers to it. As a result, the corrected salt concentration is converted to the amount of urinary salt excretion per day.

The creatinine concentration and the amount of urinary salt excretion per day, determined in the above manner, are displayed on the display 204. Upon the display of the creatinine concentration and the amount of urinary salt excretion per day on the display 204, the user may recognize that the measurement has been completed. It is preferred to store the creatinine concentration and the amount of urinary salt excretion per day in the storage unit 310 together with the time measured by the time measuring unit 308.

According to the measuring apparatus 900, based on the salt concentration corrected by using the creatinine concentration measured with high accuracy, the amount of urinary salt excretion per day may be calculated. It is therefore possible to obtain the amount of urinary salt excretion per day with high accuracy and good reproducibility.

In this embodiment, the device for measuring the amount of salt may include two or more reagent layers in the same manner as in Embodiment 1.

In this embodiment, in the same manner as in Embodiment 1, the voltage applied by the voltage application unit does not always need to be changed to a different voltage as long as a current dependent on the creatinine concentration is obtained.

In this embodiment, in the same manner as in Embodiment 1, the voltage between the first electrode and the second electrode may be any voltage at which the reduced M-PMS is oxidized.

In this embodiment, in the same manner as in Embodiment 1, the time (reaction time) from the detection of introduction of a sample to the detection of an electrical signal is not to be construed as limiting.

This embodiment has shown an example in which an electrical signal is detected five seconds after the application of a voltage between the first electrode and the second electrode, but this time is not to be construed as limiting.

This embodiment has shown an example in which the storage unit stores the first to third correlation data, but this is not to be construed as limiting. Instead, the storage unit may store correlation data indicating a correlation between electrical signals detected by the electrical signal detector, voltages detected by the voltage detector, and amounts of urinary salt excretion per unit time (e.g., per day). In this case, there is no need to determine creatinine concentration or salt concentration. The amount of urinary salt excretion per unit time may be directly determined from the electrical signal detected by the electrical signal detector and the voltage detected by the voltage detector.

In order to facilitate the introduction of a sample into the sample holding spaces of the measuring device, a lecithin layer similar to that of Embodiment 1 may be formed on the inner walls of the second substrate and the third substrate.

Also, the apparatus for measuring the amount of salt may further include a recorder for recording measurement results in a storage medium such as an SD card.

Also, the apparatus for measuring the amount of salt may further include a transmitter for transmitting measurement results to outside of the measuring apparatus.

Also, the apparatus for measuring the amount of salt may further include a receiver for receiving the results of analysis by an analytical department, an analytical laboratory, or the like.

Embodiment 4

Figure 11:
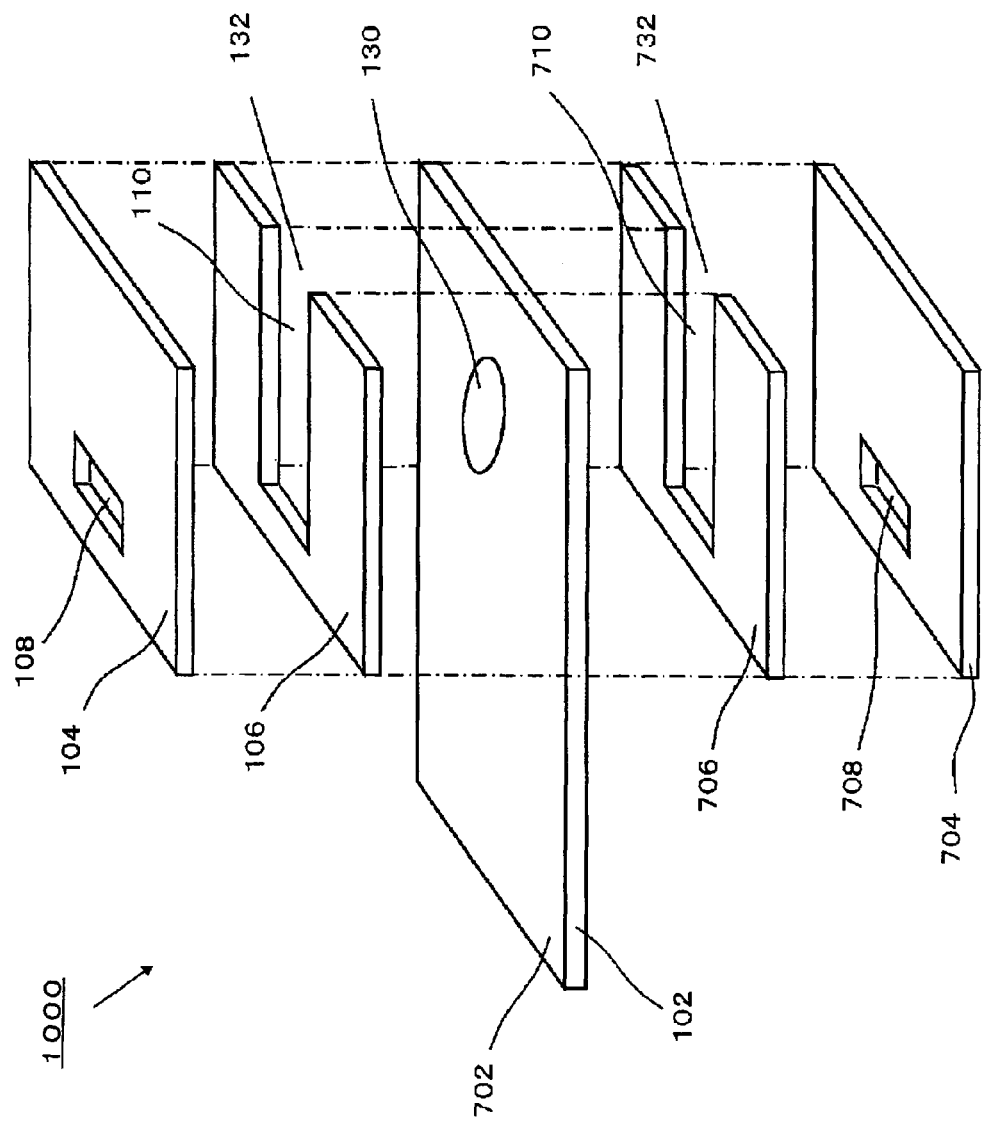
FIG. 11 is an exploded perspective view showing the structure of a device for measuring the amount of salt in Embodiment 4 of the invention seen from the first face side of the first substrate.
Figure 12:
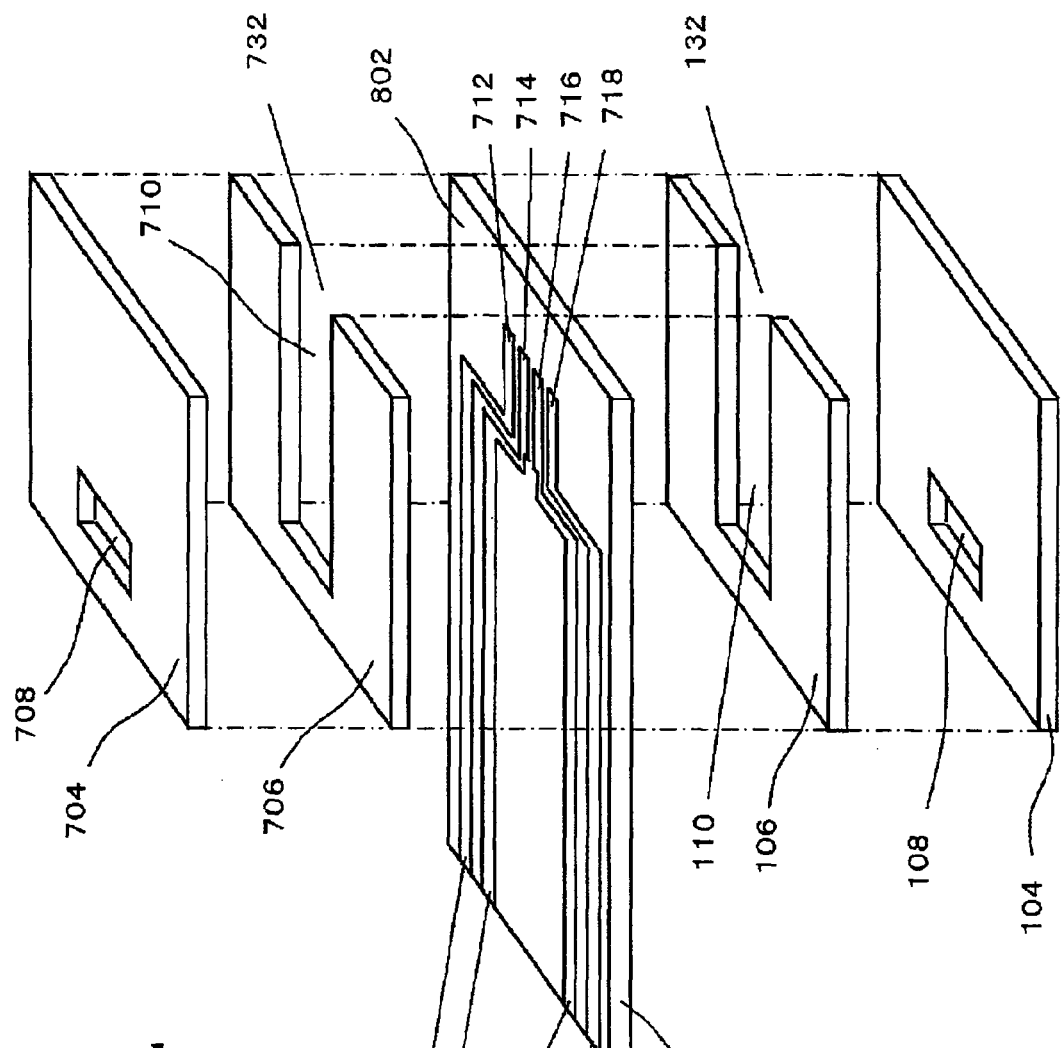
FIG. 12 is an exploded perspective view showing the structure of the device for measuring the amount of salt seen from the second face side of the first substrate in the same embodiment.

Next, a device 1000 for measuring the amount of salt according to Embodiment 4 of the invention is described with reference to FIGS. 11 and 12. FIG. 11 is an exploded perspective view showing the structure of the device 1000 for measuring the amount of salt on the first face side of the first substrate, and FIG. 12 is an exploded perspective view showing the structure on the second face side of the first substrate.

The measuring device 1000 is used in a method of optically measuring creatinine contained in urine (sample) and measuring an electrical property of the urine in order to estimate the amount of urinary salt excretion in a day from the results of these measurements.

In the measuring device 1000, a first face 702 of an insulating first substrate 102 is in contact with a first spacer 106 with a slit 110, and the first substrate 102 is combined with a second substrate 104 with an air vent 108 so as to sandwich the first spacer 106. Further, a second face 802 of the first substrate 102 is in contact with a second spacer 706 with a slit 710, and the first substrate 102 is combined with a third substrate 704 with an air vent 708 so as to sandwich the second spacer 706. The first substrate 102, the first spacer 106, the second substrate 104, the second spacer 706, and the third substrate 704 are made of, for example, polyethylene terephthalate.

In the measuring device 1000, unlike the measuring device 100 according to Embodiment 1, the first substrate 102 does not have a first electrode 112, a second electrode 114, a first lead 122, and a second lead 124. Also, a reagent layer 130, which is the same as that of Embodiment 1, is disposed on the first substrate 102, not on the first electrode 112 and the second electrode 114.

Disposed on the second face 802 of the first substrate 102 are a first electrode 712, a second electrode 714, a third electrode 716, and a fourth electrode 718. Further disposed on the second face 802 are a first lead 722 electrically connected to the first electrode 712, a second lead 724 electrically connected to the second electrode 714, a third lead 726 electrically connected to the third electrode 716, and a fourth lead 728 electrically connected to the fourth electrode 718. The dimensions of the first substrate 102 may be suitably set; for example, the width is approximately 7 mm, the length is approximately 30 mm, and the thickness is approximately 0.7 mm.

Next, the method for producing the measuring device 1000 is described.

First, the first electrode 712, the second electrode 714, the third electrode 716, the fourth electrode 718, the first lead 722, the second lead 724, the third lead 726, and the fourth lead 728 are formed in the same manner as the third to sixth electrodes and the third to sixth leads of Embodiment 3. The first electrode 712, the second electrode 714, the third electrode 716, and the fourth electrode 718 are to be electrically connected to the terminals of an apparatus for measuring the amount of salt, which will be described below, by the first lead 722, the second lead 724, the third lead 726, and the fourth lead 728, respectively.

Next, a given amount of an aqueous Solution containing a creatinine quantitative reagent, which is the same as that of Embodiment 1, is dropped on the first face 702 of the first substrate 102 by using a microsyringe or the like. Thereafter, the first substrate 102 is left for drying in an environment at room temperature to approximately 30° C., to form the reagent layer 130. The concentration and amount of the reagent containing aqueous solution to be applied thereto may be selected depending on the characteristics and size of the necessary device; for example, they may be selected in the same manner as in Embodiment 1.

Subsequently, the second substrate 104, the first spacer 106, the first substrate 102, the second spacer 706, and the third substrate 704 are combined so that the first face 702 of the first substrate 102 contacts the first spacer 106 and the second face 802 of the first substrate 102 contacts the second spacer 706. Adhesive is applied to the portions of the respective components to be bonded, and they are laminated, pressed, and allowed to stand for bonding. Instead of this method, it is also possible to combine them without applying adhesive and then thermally or ultrasonically bond the bonding portions by using a commercially available welding machine.

When the first substrate 102, the first spacer 106, and the second substrate 104 are combined, a space is formed by the slit 110 of the first spacer 106 between the first substrate 102 and the second substrate 104, and this space serves as a first sample holding space for measuring creatinine concentration. Also, the opening of the slit 110 serves as a first sample inlet 132 for measuring creatinine concentration.

When the first substrate 102, the second spacer 706, and the third substrate 704 are combined, a space is formed by the slit 710 of the second spacer 706 between the first substrate 102 and the third substrate 704, and this space serves as a second sample holding space for measuring an electrical property of urine. Also, the opening of the slit 710 serves as a second sample inlet 732 for measuring an electrical property of urine.

Figure 13:
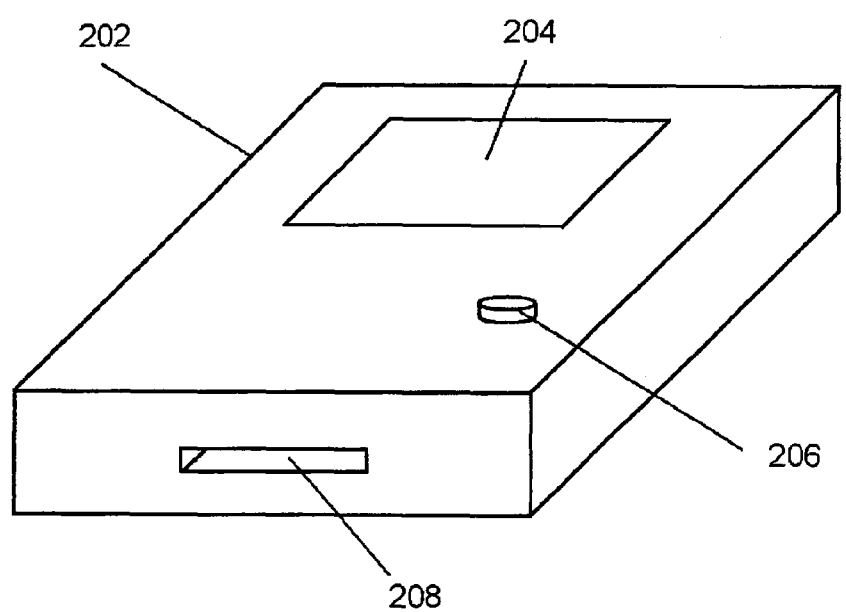
FIG. 13 is a perspective view showing the appearance of an apparatus for measuring the amount of salt in the same embodiment.
Figure 14:
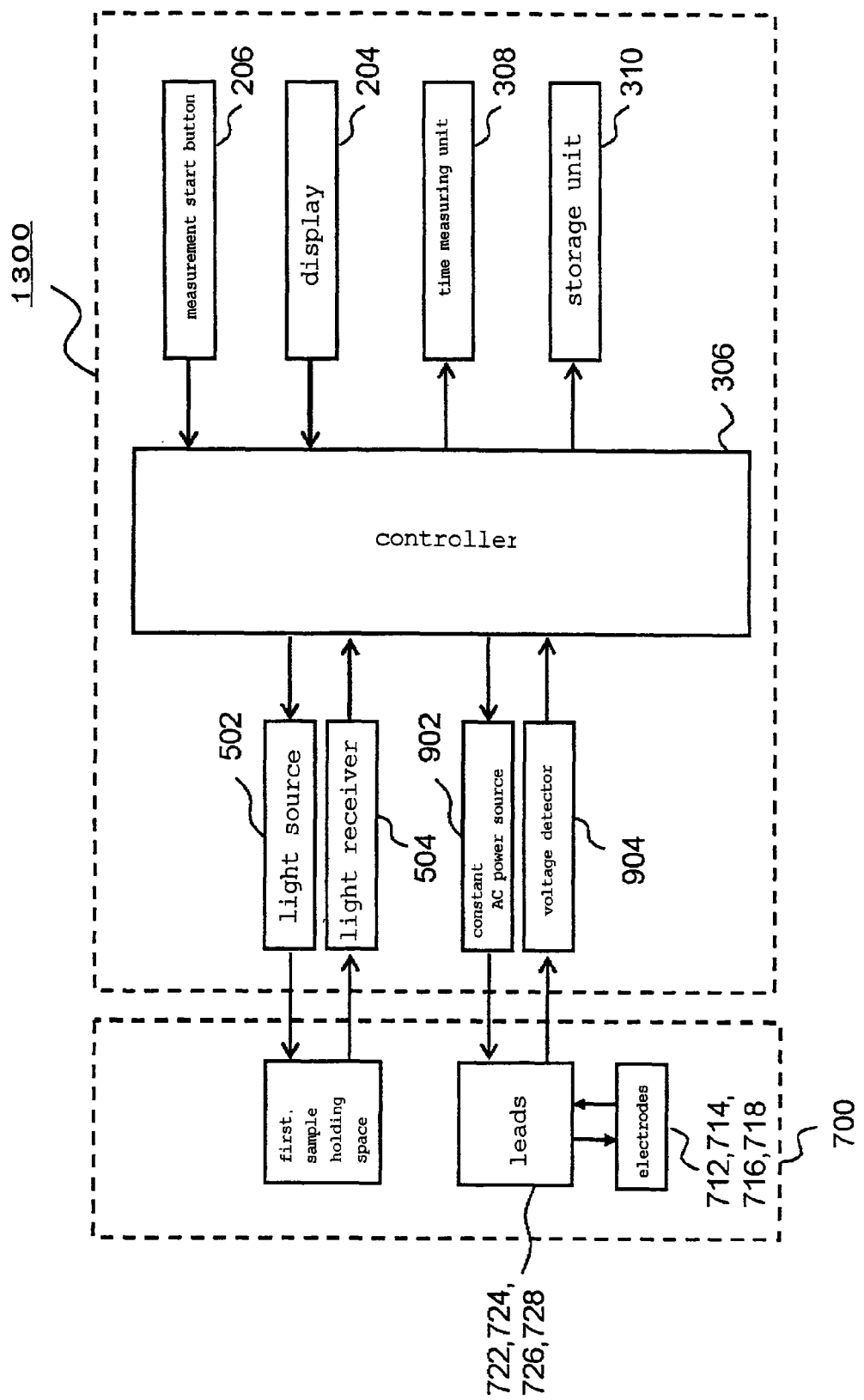
FIG. 14 is a block diagram showing the configuration of the apparatus for measuring the amount of salt in the same embodiment.

Next, an apparatus 1300 for measuring the amount of salt according to this embodiment and the method for measuring the amount of salt using this apparatus are described with reference to FIGS. 13 and 14. FIG. 13 is a perspective view showing the appearance of the measuring apparatus 1300, and FIG. 14 is a block diagram showing the configuration of the measuring apparatus 1300.

First, the structure of the measuring apparatus 1300 is described with reference to FIG. 13.

A housing 202 of the measuring apparatus 1300 has a measuring device mounting port 208 for mounting the measuring device 1000, a display 204 for displaying measurement results etc., and a measurement start button 206 for starting the measurement of creatinine concentration and an electrical property of urine by the measuring apparatus 900. Inside the measuring device mounting port 208 are a first terminal, a second terminal, a third terminal, and a fourth terminal, which are to be electrically connected to the first lead 722, the second lead 724, the third lead 726, and the fourth lead 728 of the measuring device 1000, respectively.

Next, the configuration inside the housing 202 of the measuring apparatus 1300 is described with reference to FIG. 14.

The housing 202 of the measuring apparatus 1300 contains a light source 502, a light receiver 504, a constant AC power source 902, a voltage detector 904, a controller 306, a time measuring unit 308, and a storage unit 310.

The light source 502 has the function of emitting light to the first sample holding space of the measuring device 1000 mounted in the measuring device mounting port 208. The wavelength of the light emitted from the light source 502 may be selected in the same manner as in Embodiment 2.

The light receiver 504 has the function of detecting the light emitted from the light source 502 and reflected from the first sample holding space of the measuring device 1000.

The constant AC power source 902 has the function of applying a constant alternating current between the first electrode 712 and the fourth electrode 718 of the measuring device 1000 through the first terminal and the fourth terminal. The alternating current applied has, for example, a frequency of approximately 1 kHz and a current value of approximately 0.1 mA.

The voltage detector 904 has the function of detecting the voltage (effective value of alternating voltage) between the second electrode 714 and the third electrode 716 through the second terminal and the third terminal.

The storage unit 310 stores first correlation data corresponding to a first calibration curve which indicates a correlation between creatinine concentrations and reflected light intensities detected by the light receiver 504. The storage unit 310 also stores second correlation data corresponding to a second calibration curve and third correlation data corresponding to a third calibration curve which are the same as those of the storage unit 310 of Embodiment 3.

The controller 306 has the functions of:

(I) converting the intensity of reflected light detected by the light receiver 504 to creatinine concentration by referring to the first correlation data;

(II) converting the voltage detected by the voltage detector 904 to salt concentration by referring to the second correlation data;

(III) correcting the salt concentration by using the creatinine concentration thus obtained; and (IV) converting the corrected salt concentration to the amount of urinary salt excretion per day by referring to the third correlation data.

Next, the method for measuring the amount of salt using the measuring device 1000 and the measuring apparatus 1300 according to this embodiment is described.

First, a user inserts the lead side of the measuring device 1000 into the measuring device mounting port 208 of the measuring apparatus 1300. As a result, the first lead 722, the second lead 724, the third lead 726, and the fourth lead 728 of the measuring device 1000 are electrically connected to the first terminal, the second terminal, the third terminal, and the fourth terminal inside the measuring device mounting port 208, respectively.

When the measuring device 1000 is inserted into the measuring device mounting port 208, an insertion detecting switch is turned on, so that a signal is sent to the controller 306. The insertion detecting switch comprises a microswitch installed in the measuring device mounting port 208. When the controller 306 detects the insertion of the measuring device 1000 from the signal sent from the insertion detecting switch, the controller 306 actuates the light source 502. As a result, light is emitted to the first sample holding space of the measuring device 700 from the light source 502.

Subsequently, the user brings a sample into contact with the first sample inlet 132 and the second sample inlet 732 of the measuring device 1000. Due to this contact, the sample is sucked into the two sample holding spaces of the measuring device 1000 from the first sample inlet 132 and the second sample inlet 732 by capillarity, so that the two sample holding spaces are filled with the sample. When the sample reaches the position of the first sample holding space to which the light is emitted, the transmittance inside the sample holding space changes. The resulting change in the intensity of reflected light is detected by the light receiver 504.

When the controller 306 detects the introduction of the sample into the first and second sample holding spaces from the signal sent from the light receiver 504, the controller 306 causes the time measuring unit 308, which is a timer, to start measuring time.

Upon the detection of introduction of the sample into the second sample holding space, the controller 306 controls the constant AC power source 902, so that a constant alternating current (e.g., frequency 1 kHz, current value 0.1 mA) is applied between the first electrode 712 and the fourth electrode 718 through the first terminal and the fourth terminal. After a predetermined time (e.g., after five seconds) from the application of the alternating current, the voltage detector 904 measures the voltage (effective value of alternating voltage) between the second electrode 714 and the third electrode 716.

The controller 306 reads the second correlation data stored in the storage unit 310 and refers to it. As a result, the voltage detected by the voltage detector 904 is converted to the salt concentration in the sample.

When the sample comes into contact with the reagent layer 130 in the first sample holding space, M-PMS contained in the reagent layer 130 dissolves in the sample. The dissolved M-PMS in the sample directly reacts with creatinine contained in the sample, thereby forming reaction products (an oxidation product of creatinine and reduced M-PMS). The reduction of the M-PMS causes a change in the absorption spectrum of the sample.

When the controller 306 determines from the signal sent from the time measuring unit 308 that a predetermined time (e.g., 60 seconds) has passed, it causes the light receiver 504 to measure the intensity of the light reflected from the sample holding space. The intensity of the reflected light measured by the light receiver 504 is dependent on the concentration of creatinine contained in the sample.

The controller 306 reads the first correlation data stored in the storage unit 310 and refers to it. As a result, the intensity of the reflected light detected by the light receiver 504 is converted to the creatinine concentration in the sample.

Thereafter, the controller 306 corrects the salt concentration by using the creatinine concentration obtained. The controller 306 then reads the third correlation data stored in the storage unit 310 and refers to it. As a result, the corrected salt concentration is converted to the amount of urinary salt excretion per day. The creatinine concentration and the amount of urinary salt excretion per day, determined in the above manner, are displayed on the display 204.

According to the measuring apparatus 1300, based on the salt concentration corrected by using the creatinine concentration measured with high accuracy, the amount of urinary salt excretion per day may be calculated. It is therefore possible to obtain the amount of urinary salt excretion per day with high accuracy and good reproducibility.

In this embodiment, the measuring device may include two or more reagent layers in the same manner as in Embodiment 1.

Also, in this embodiment, in the same manner as in Embodiment 2, the time from the detection of introduction of a sample to the detection of reflected light intensity is not to be construed as limiting.

Also, in this embodiment, the storage unit may store correlation data indicating a correlation between reflected light intensities detected by the light receiver, voltages detected by the voltage detector, and amounts of urinary salt excretion per unit time (e.g., per day) instead of the first to third correlation data. In this case, there is no need to determine creatinine concentration or salt concentration. The amount of urinary salt excretion per unit time may be directly determined from the intensity of the reflected light detected by the light receiver and the voltage detected by the voltage detector.

In order to facilitate the introduction of a sample into the sample holding spaces of the measuring device, a lecithin layer similar to that of Embodiment 1 may be formed on the inner walls of the second substrate and the third substrate.

Also, the measuring apparatus may further include a recorder for recording measurement results in a storage medium such as an SD card.

Also, the measuring apparatus may further include a transmitter for transmitting measurement results to outside of the measuring apparatus.

Also, the measuring apparatus may further include a receiver for receiving the results of analysis by an analytical department, an analytical laboratory, or the like.

EXAMPLES

Example 1

The following experiment was conducted to confirm the effect of the method for measuring creatinine concentration according to the invention.

First, an aqueous solution of 100 mM dipotassium hydrogen phosphate (available from Wako Pure Chemical Industries, Ltd.; this was also used in the following examples and reference examples) and an aqueous solution of 100 mM potassium dihydrogen phosphate (available from Wako Pure Chemical Industries, Ltd.; this was also used in the following examples and reference examples) were prepared. While monitoring with a pH meter, the two aqueous solutions were alternately mixed to adjust the pH of the resultant mixed aqueous solution to 7. In this way, a 100 mM phosphate buffer solution (pH=7) was prepared. In this buffer solution was dissolved M-PMS (available from DOJINDO LABORATORIES; this was also used in the following) at a concentration of 10 mM.

The aqueous solution thus obtained was introduced into a glass cell container, and a first electrode, a second electrode, and a third electrode were immersed in the aqueous solution in the cell container. The first electrode was a gold electrode (electrode area 2 mm$^2$). The second electrode was prepared by winding up a 5-cm long platinum wire in a coil. The third electrode was an Ag/AgCl (saturated KCl aqueous solution) reference electrode. All the electrodes are commercial products available from BAS Inc. The connecting terminals of the first electrode, the second electrode, and the third electrode were sequentially connected to the connecting terminals of the working electrode, counter electrode, and reference electrode of an electrochemical analyzer (ALS-660A available from ALS Co., Ltd.).

Subsequently, a small amount of a creatinine aqueous solution with a concentration of 500 mM (available from Wako Pure Chemical Industries, Ltd.; this was also used in the following examples and reference examples) was added to the aqueous solution in the cell container. The amount of the creatinine aqueous solution added was adjusted in each measurement so that the concentration of creatinine contained in the aqueous solution in the cell container was a predetermined value.

Upon the addition of creatinine, time measurement was started, and 10 minutes after the addition of creatinine, a potential of 0.6 V was applied to the first electrode relative to the third electrode. Five seconds after the potential application, the current value was measured. This experiment was conducted at room temperature (approximately 25° C.)

The creatinine concentration in the aqueous solution contained in the cell container was varied to 0, 6, 18, 27, and 54 mM, and measurements were made in the manner as described above.

Figure 15:
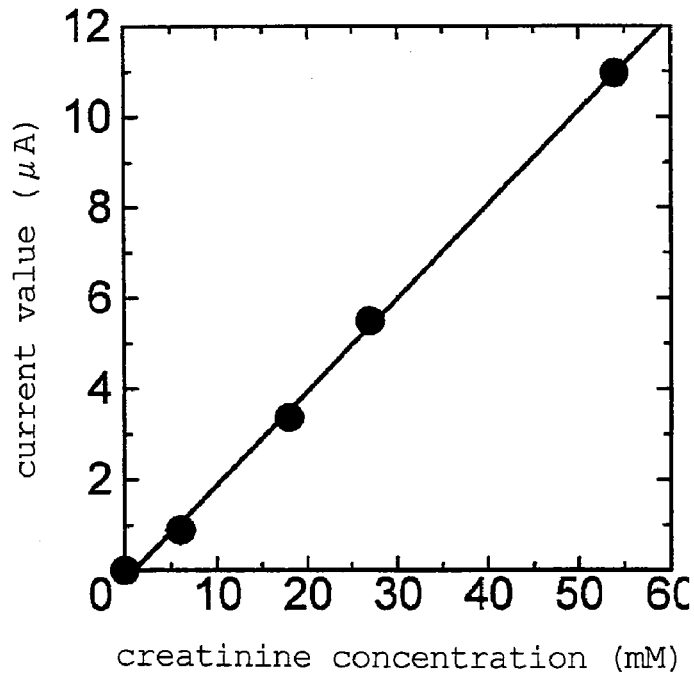
FIG. 15 is a graph showing the relationship between the creatinine concentration in a sample and the current value measured in Example 1 of the invention.

FIG. 15 is a graph of the measured current values plotted as a function of creatinine concentration. In FIG. 15, the abscissa represents the concentration (mM) of creatinine contained in the aqueous solution in the cell container, and the ordinate represents the measured current values (μA). As is clear from FIG. 15, the current value increases linearly with (i.e., in proportion to) the increase in creatinine concentration in the aqueous solution in the cell container, which indicates a high correlation between the current values and the creatinine concentrations. Therefore, it is understood that the method for measuring creatinine concentration according to the invention may provide creatinine quantification based on current values obtained.

From the above results, the reactions in the creatinine concentration measuring method of the invention may be explained as follows.

In the sample, M-PMS reacts with creatinine in the presence of a phosphate buffer, thereby being reduced. That is, in this reaction, creatinine donates electrons to M-PMS, thereby being oxidized. The first electrode is under such a potential that electrons are received from the reduced M-PMS. Thus, the reduced M-PMS is electrochemically oxidized at the first electrode. As a result, a current flows through the first electrode. The concentration of M-PMS reduced in a certain time is dependent on the creatinine concentration. Also, the oxidation current of the reduced M-PMS is dependent on the concentration or amount of the reduced M-PMS in the sample. Therefore, the current value obtained is dependent on the creatinine concentration.

Example 2

Next, the following experiment was conducted to check the pH range preferable in the method for measuring creatinine concentration according to the invention. Since the method for preparing samples used in the experiment, the structure of the apparatus used, and the experiment procedure are the same as those of Example 1, the explanation thereof is omitted. However, in this example, the concentration of the buffer solution was set to 400 mM, and the creatinine concentration in the sample was set to 27 mM. Also, the pH of the phosphate buffer solution added to the sample was varied to 2, 3, 4, 5, 6, 7, 8, 9, 10, 11, 12, and 13, and measurements were made in the same manner as in Example 1.

Figure 16:
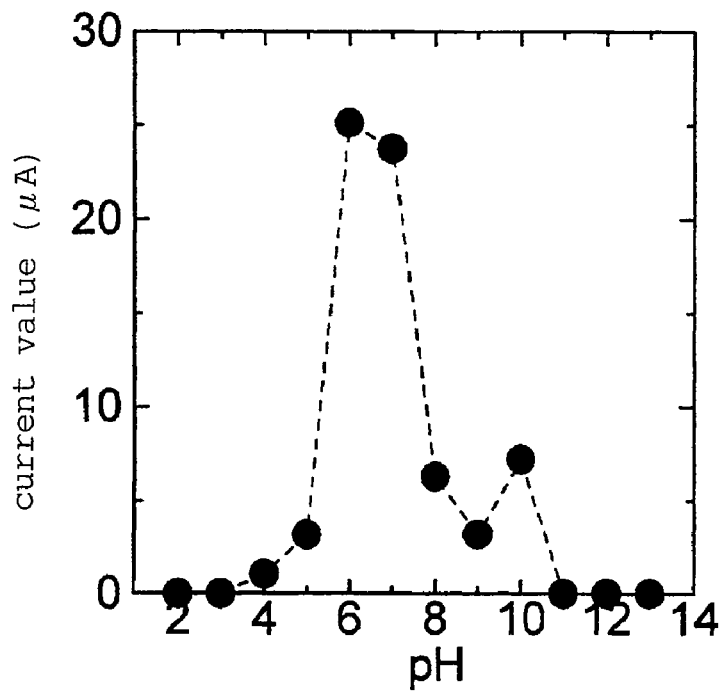
FIG. 16 is a graph showing the relationship between the pH of a sample and the current value measured in Example 2 of the invention.

FIG. 16 shows the measurement results of current values. In the pH range of 5 to 10, the current value is equal to or greater than 1 μA. In the pH range of 6 to 7, the current value is significantly high and the current value is stable. This result shows that in this pH range, creatinine may be quantified with particularly high sensitivity and high reproducibility. The pH range of 6 to 7 is achieved by using the hydrogen phosphate ion and the dihydrogen phosphate ion. It is thus thought that the preferable phosphate buffer comprises, for example, a combination of dipotassium hydrogen phosphate or disodium hydrogen phosphate and potassium dihydrogen phosphate or sodium dihydrogen phosphate.

Example 3

First, an aqueous solution of 50 mM dipotassium hydrogen phosphate and an aqueous solution of 50 mM potassium dihydrogen phosphate were prepared. While monitoring with a pH meter, the two aqueous solutions were alternately mixed to adjust the pH of the resultant mixed aqueous solution to 7. In this way, a 50 mM phosphate buffer solution (pH=7) was prepared. In this buffer solution was dissolved M-PMS at a concentration of 10 mM.

Subsequently, to the resultant M-PMS aqueous solution was added a small amount of a creatinine aqueous solution with a concentration of 500 mM. The amount of the creatinine aqueous solution added was adjusted in each measurement so that the concentration of creatinine contained in the M-PMS aqueous solution was a predetermined value.

The aqueous solution thus obtained was introduced as a sample into a glass cell container. Using an absorptiometer (available from Shimadzu Corporation, model: MultiSpec-1500), the absorption spectrum in the wavelength range of 400 to 800 nm was measured. The absorption spectrum was measured 1, 5, 10, 15, 20, 30, 40, 60, and 80 minutes after the addition of creatinine. This experiment was conducted at room temperature (approximately 25° C.).

The creatinine concentration in the aqueous solution contained in the cell container was varied to 0, 10, 20, and 40 mM, and measurements were made in the manner as described above.

Figure 17:
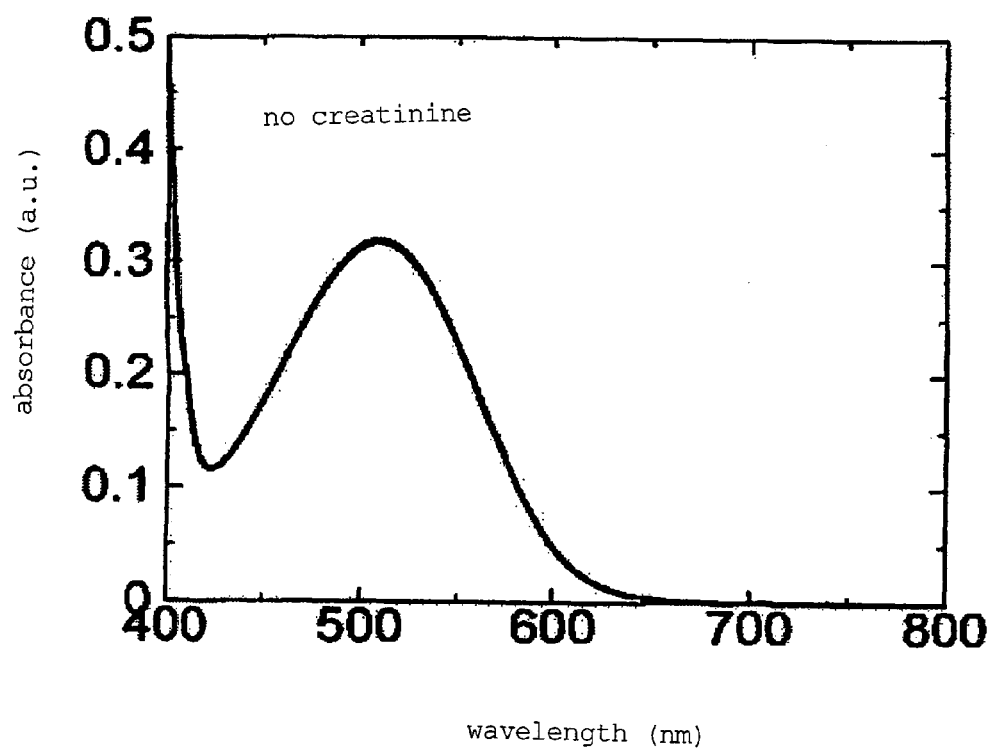
FIG. 17 is a graph showing a change with time in the absorption spectrum of a sample with a creatinine concentration of 0 mM measured in Example 3 of the invention.
Figure 18:
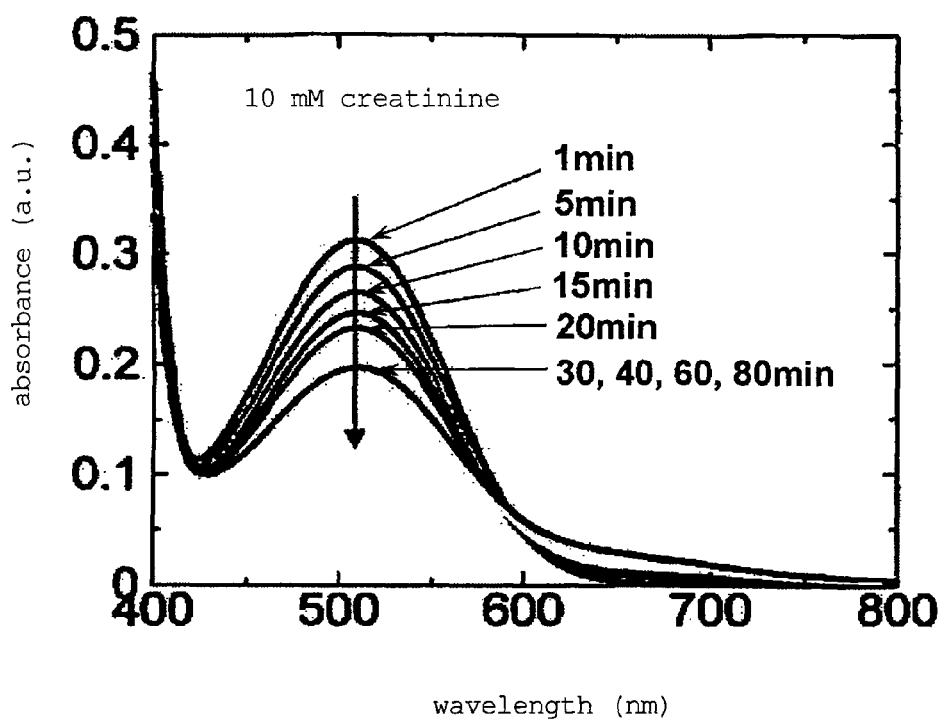
FIG. 18 is a graph showing a change with time in the absorption spectrum of a sample with a creatinine concentration of 10 mM in the same Example.
Figure 19:
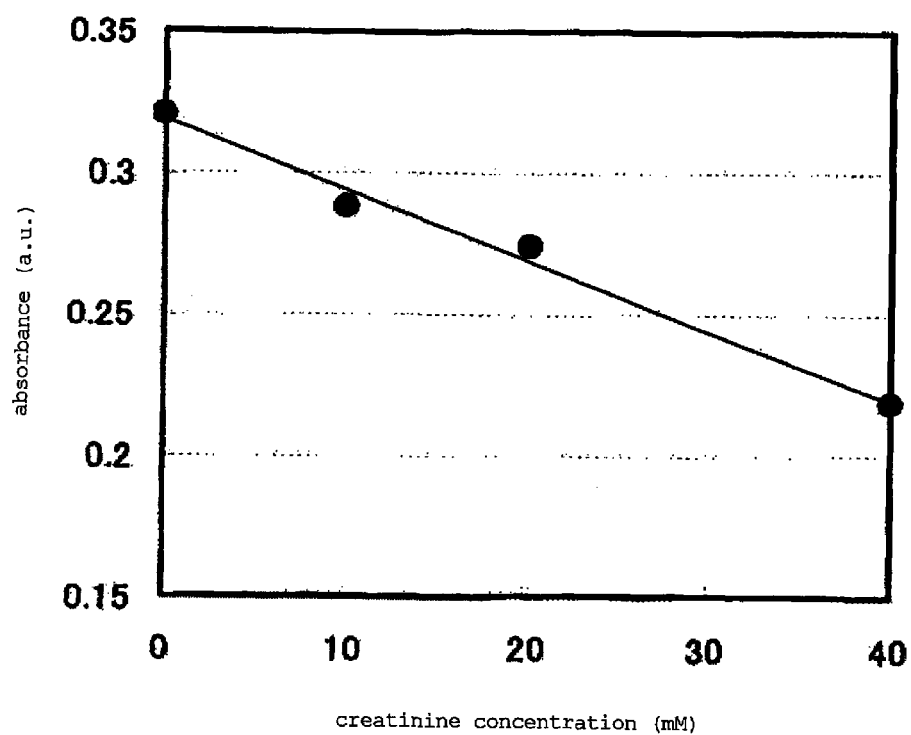
FIG. 19 is a graph showing the relationship between the absorbance at a wavelength of 510 nm measured five minutes after the addition of creatinine and the creatinine concentration in the sample in the same Example.

The measurement results are described with reference to FIGS. 17 to 19. FIG. 17 is a graph showing a change with time in the absorption spectrum of a sample with a creatinine concentration of 0 mM. FIG. 18 is a graph showing a change with time in the absorption spectrum of a sample with a creatinine concentration of 10 mM. FIG. 19 is a graph showing the relationship between the absorbance at a wavelength of 510 nm measured five minutes after the addition of creatinine and the creatinine concentration in the sample. In FIG. 17 and FIG. 18, the abscissa represents wavelength (nm), and the ordinate represents absorbance (arbitrary intensity). In FIG. 19, the abscissa represents the creatinine concentration in the sample (mM), and the ordinate represents the absorbance (arbitrary intensity) at a wavelength of 510 nm.

As is clear from FIG. 17, in the sample containing no creatinine, there is no change with time in absorption spectrum. Contrary to this, as can be seen from FIG. 18, in the sample containing creatinine, the intensity of the absorption peak near the wavelength of 510 nm decreases with increasing time after the addition of creatinine. Also, approximately 30 minutes after the addition of creatinine, the change of the peak intensity becomes saturated. Thus, the absorbance at the wavelength of 510 nm measured five minutes after the addition of creatinine was plotted as a function of the creatinine concentration in the sample, and this plot is shown in FIG. 19. That is, the absorbance obtained decreases linearly with the increase in the creatinine concentration in the sample, thus exhibiting a high correlation between the absorbance and the creatinine concentration. Therefore, it is understood that the method for measuring creatinine concentration according to the invention may provide creatinine quantification based on absorbances obtained.

Reference Example 1

The following experiment was conducted to confirm the effect of stabilizing M-PMS. In this reference example, sodium methyl sulfate, sodium nitrate, and sodium chloride were used as electrolyte salts of a monovalent anion.

In this reference example, samples were prepared as follows. First, an aqueous solution of 1M dipotassium hydrogen phosphate and an aqueous solution of 1M potassium dihydrogen phosphate were prepared. Next, while monitoring with a pH meter, the two aqueous solutions were alternately mixed to adjust the pH of the resultant mixed aqueous solution to 6. The phosphate buffer solution (pH=6) thus obtained and an aqueous solution of an electrolyte salt of a monovalent anion were mixed so that the final concentrations thereof were 400 mM and 800 mM, respectively. Lastly, an M-PMS aqueous solution was added to the resultant mixed aqueous solution so that the final concentration thereof was 100 mM. In this way, the samples of this reference example were prepared.

Also, a reference sample was prepared in the same manner except that an electrolyte salt of a monovalent anion was not added.

Every minute after the addition of M-PMS, 0.6 μL of the sample was collected and charged into an electrochemical sensor chip, and an electrochemical measurement was conducted. The electrochemical sensor chip used was a sensor chip (trade name: G sensor) available from ARKRAY Inc. Before the sensor chip was used, it was ultrasonically cleaned in pure water for five minutes to remove the reagent in the sensor chip. The electrodes of the sensor chip are made of palladium. The first palladium electrode and the second palladium electrode in the sensor chip were sequentially connected to the connecting terminals of working and reference electrodes of an electrochemical analyzer (ALS-700A available from ALS Co., Ltd.). The electrochemical measurement was made by applying a potential of 400 mV to the first electrode relative to the second electrode for five seconds immediately after the introduction of a sample, and measuring the current flowing five seconds after the start of the application. The reaction was carried out at room temperature (approximately 25° C.).

Figure 20:
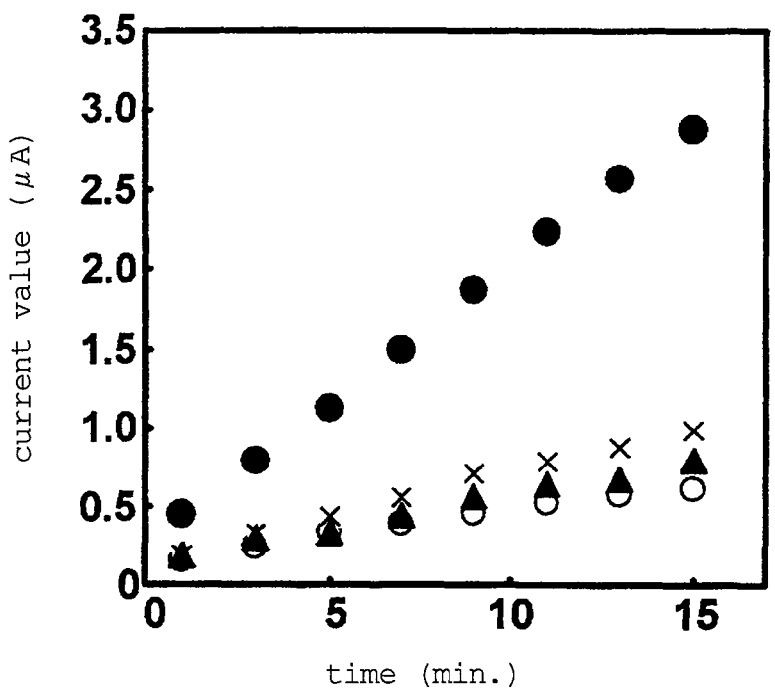
FIG. 20 is a graph showing a change with time in the oxidation current value measured on samples of Reference Example 1 and a reference sample.

FIG. 20 is a graph showing a change with time in the oxidation current values measured on the samples of this reference example and the reference sample. In FIG. 20, the black circles represent data on the reference sample, the white circles represent data on the addition of sodium methyl sulfate, the black triangles represent data on the addition of sodium nitrate, and the x signs represent data on the addition of sodium chloride.

In the case of the reference sample, a linear increase in oxidation current value in proportion to the passage of time was observed. On the other hand, in the case of the samples to which sodium methyl sulfate, sodium nitrate, or sodium chloride was added as an electrolyte salt of a monovalent anion, an increase in current value was suppressed even after 15 minutes. This confirmed that M-PMS was stable in the phosphate buffer solution. Also, as can be understood from FIG. 20, the effect of suppressing an increase in current value was greatest in the sample where the electrolyte salt of a monovalent anion was sodium methyl sulfate.

The above results demonstrate that the addition of an electrolyte salt of a monovalent anion stabilizes M-PMS in a phosphate buffer solution. Such electrochemical response was also observed in the case of using a common electrochemical measurement system such as a three-electrode batch type using a working electrode, a counter electrode, and a reference electrode, without being limited to the sensor chip used in this example. Also, the electrode material is not limited to palladium, and similar behavior is observed in the case of using electrode materials such as glassy carbon, gold, and platinum.

Example 4

Next, the following experiment was conducted to check the influence of the reagent composition according to the invention on the measurement of creatinine concentration. In this example, sodium methyl sulfate was used as an electrolyte salt of a monovalent anion.

In this example, five samples with creatinine concentrations of 0, 10.8, 21.6, 42.3, and 54 mM were prepared by adding a creatinine aqueous solution to samples prepared in the same manner as in Reference Example 1. Also, a reference sample was prepared in the same manner except that an electrolyte salt of a monovalent anion was not added. The current value was measured using the same sensor chip and measuring apparatus as those of Reference Example 1.

Figure 21:
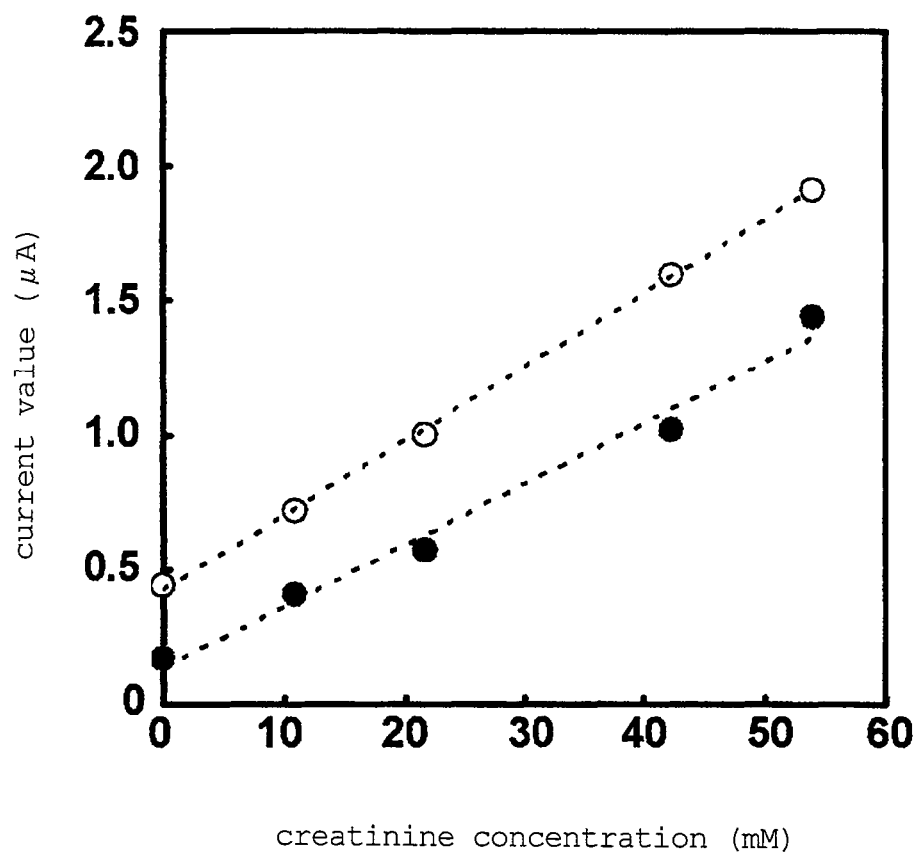
FIG. 21 is a graph showing the relationship between the current value measured and the creatinine concentration in samples in Example 4 of the invention.

FIG. 21 is a graph showing the relationship between the current values measured in this example and the concentration of creatinine contained in the sample. In FIG. 21, the black circles represent data on this example, and the white circles represent data on the reference sample.

In the case of the reference sample, an increase in current value commensurate with the increase in creatinine concentration was observed. On the other hand, in the case of the samples of this example, although the current value decreased compared with the reference sample, an increase in oxidation current value commensurate with the creatinine concentration was observed. Between the samples of this example and the reference sample, no difference was observed in the slope of the current value relative to the creatinine concentration. The above results confirm that sodium methyl sulfate, which is an electrolyte salt of a monovalent anion, contributes to only improving the instability of M-PMS, and has no effect on the reaction between M-PMS and creatinine.

The above results may be explained as follows. In the phosphate buffer solution, the reaction between creatinine and M-PMS is promoted, resulting in formation of a reaction product. The reaction product is oxidized by the first electrode to produce a current. Since the resulting current value is dependent on the concentration of reacted creatinine, the detection of creatinine is achieved. However, in the reference sample, M-PMS becomes unstable due to the phosphate ion, resulting in formation of unstable products, which increase the oxidation current value. In this example, the presence of sodium methyl sulfate as an electrolyte salt of a monovalent anion resolves the instability of M-PMS, thereby eliminating the increase in oxidation current value due to unstable products. Sodium methyl sulfate, however, does not inhibit the reaction between M-PMS and creatinine.

Reference Example 2

The following experiment was conducted to examine the effect of improving measurement reproducibility according to the invention. In this reference example, sodium methyl sulfate and sodium nitrate were used as electrolyte salts of a monovalent anion.

In this reference example, while the M-PMS concentration was fixed to 100 mM, the concentration of the electrolyte salt of a monovalent anion and the concentration of the phosphate buffer were changed to change the ion composition of samples. Using the prepared samples and the same sensor chip and measuring apparatus as those of Reference Example 1, the current value one minute after the addition of M-PMS was measured. A potential of 400 mV was applied to the first electrode relative to the second electrode for five seconds, and the current value five seconds after the start of the application was measured. This measurement was conducted on three samples of the same conditions, and the variation in obtained values was evaluated as coefficient of variation (hereinafter abbreviated as CV value).

Figure 22:
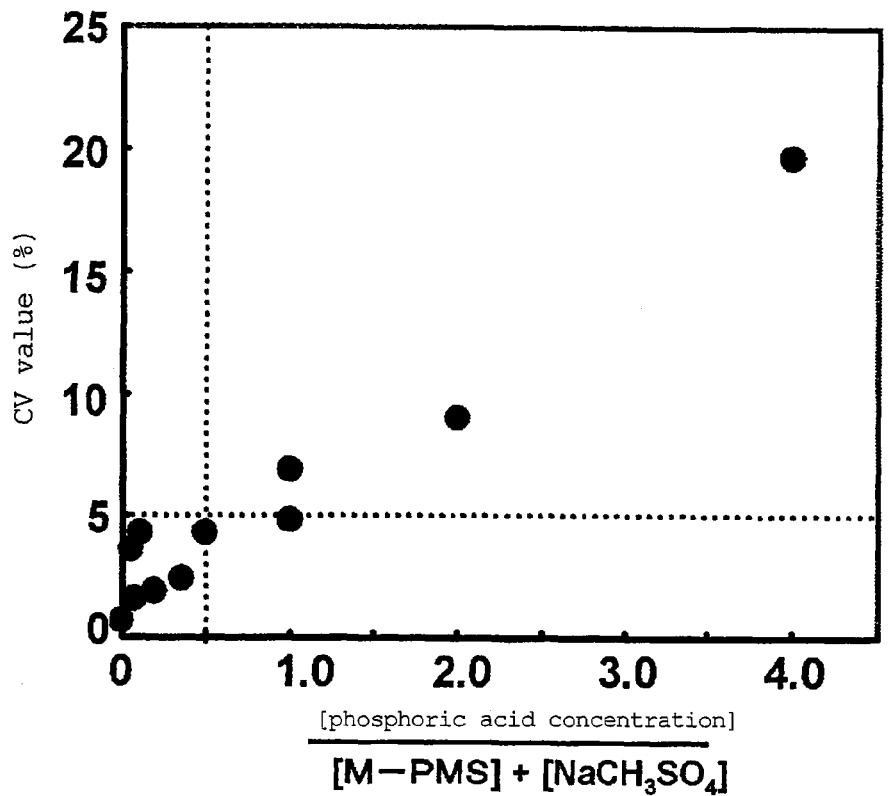
FIG. 22 is a graph showing the relationship between the CV value obtained when sodium methyl sulfate was used as an electrolyte salt of a monovalent anion and the ratio of the phosphate buffer concentration to the total of the M-PMS concentration and the electrolyte salt concentration in Reference Example 2.
Figure 23:
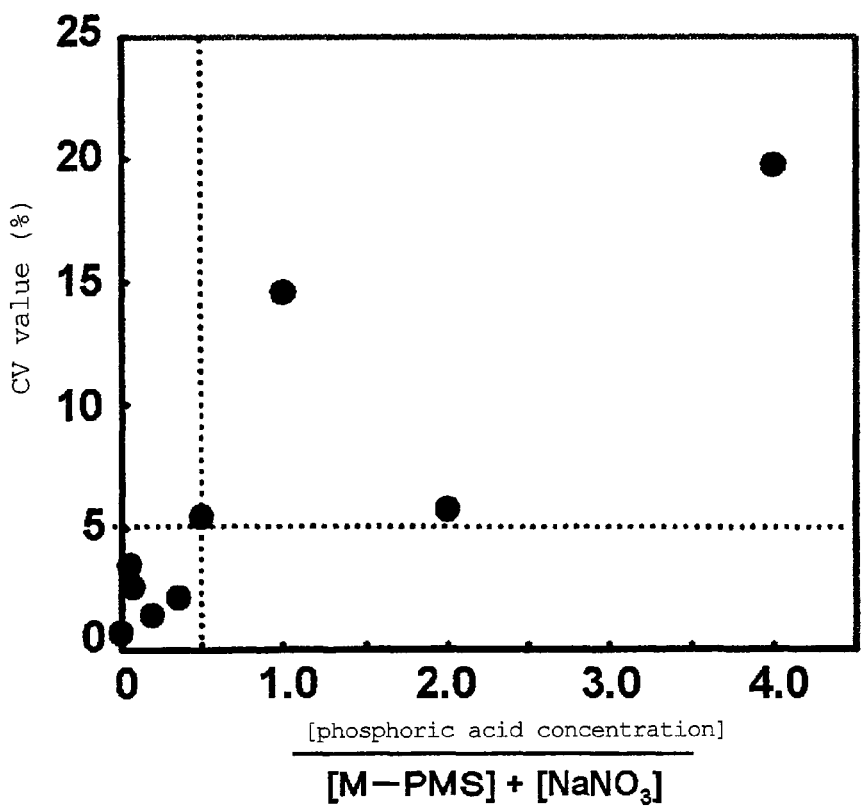
FIG. 23 is a graph showing the relationship between the CV value obtained when sodium nitrate was used as an electrolyte salt of a monovalent anion and the ratio of the phosphate buffer concentration to the total of the M-PMS concentration and the electrolyte salt concentration in the same Reference Example.

FIG. 22 is a graph showing the relationship between the CV values obtained when sodium methyl sulfate was used as an electrolyte salt of a monovalent anion and the ratio of the phosphate buffer concentration (the concentration of phosphorus atoms) to the total of the M-PMS concentration and the electrolyte salt concentration. FIG. 23 is a graph showing the relationship between the CV values obtained when sodium nitrate was used as an electrolyte salt of a monovalent anion and the ratio of the phosphate buffer concentration (the concentration of phosphorus atoms) to the total of the M-PMS concentration and the electrolyte salt concentration. As can be understood from FIGS. 22 and 23, the variation in the value of the oxidation current of M-PMS increased with the increase in the concentration of the phosphate buffer solution relative to the total of the M-PMS concentration and the electrolyte salt concentration in the solution. The variation in the value of the oxidation current of M-PMS was successfully reduced by increasing the amount of the electrolyte salt of a monovalent anion added and thus increasing the concentration of the electrolyte salt of a monovalent anion in the solution. Further, when the total of the M-PMS concentration and the electrolyte salt concentration was equal to or greater than twice the concentration of the phosphate buffer, the variation in the value of the oxidation current of M-PMS fell within 5%. When the variation in the value of the oxidation current of M-PMS in a solution containing no creatinine is within 5%, such a sensor using M-PMS has sufficient reliability for measuring creatinine. Therefore, it has been found that such a reagent composition that the total of the M-PMS concentration and the electrolyte salt concentration is equal to or greater than twice the phosphate buffer is optimum.

The above results have confirmed that the addition of an electrolyte salt which will give a monovalent anion to a reagent composition comprising M-PMS and a phosphate buffer promotes the stability of M-PMS. They have confirmed that the amount of the electrolyte salt added is sufficient if the amount of the phosphate buffer contained in the reagent composition is equal to or less than half the total of the amount of the electrolyte salt of a monovalent anion and the amount of M-PMS.

INDUSTRIAL APPLICABILITY

The invention is useful in the quantification of creatinine contained in a sample, in particular, a biological sample such as urine.

REFERENCE SIGNS LIST 100, 400 Device for Measuring Creatinine Concentration
102 First Substrate
104 Second Substrate
106 Spacer (First Spacer)
108, 708 Air Vent
110, 710 Slit
112 First Electrode
114 Second Electrode
122 First Lead
124 Second Lead
130 Reagent Layer
132 Sample Inlet (First Sample Inlet)
200, 500 Apparatus for Measuring Creatinine Concentration
202 Housing
204 Display
206 Measurement Start Button
208 Measuring Device Mounting Port
302 Voltage Application Unit
304 Electrical Signal Detector
306 Controller
308 Time Measuring Unit
310 Storage Unit
502 Light Source
504 Light Receiver
700, 1000 Device for Measuring the Amount of Salt
702 First Face
704 Third Substrate
706 Second Spacer
712 First Electrode or Third Electrode
714 Second Electrode or Fourth Electrode
716 Third Electrode or Fifth Electrode
718 Fourth Electrode or Sixth Electrode
722 First Lead or Third Lead
724 Second Lead or Fourth Lead
726 Third Lead or Fifth Lead
728 Fourth Lead or Sixth Lead
732 Second Sample Inlet
802 Second Face
900, 1300 Apparatus for Measuring the Amount of Salt
902 Constant AC power source
904 Voltage Detector

The invention claimed is:

1. A method for measuring a concentration of creatinine, comprising the steps of:

(A) mixing a sample containing creatinine with a creatinine quantitative reagent including 1-methoxy-5-methylphenazinium in the absence of either picric acid or any enzyme responsive to creatinine, to cause the creatinine to reduce the 1-methoxy-5-methylphenazinium;

(B) electrochemically or optically measuring an amount of the 1-methoxy-5-methylphenazinium reduced in the step (A); and (C) determining a concentration of the creatinine contained in the sample from the amount of the reduced 1l-methoxy-5-methylphenazinium measured in the step (B).

2. The method for measuring a concentration of creatinine in accordance with claim 1, wherein in the step (A), the sample has a pH of 5 or more and 10 or less.

3. The method for measuring a concentration of creatinine in accordance with claim 2, wherein in the step (A), the sample has a pH of 6 or more and 7 or less.

4. The method for measuring a concentration of creatinine in accordance with claim 1, wherein the creatinine quantitative reagent further contains a methyl sulfate anion.

5. The method for measuring a concentration of creatinine in accordance with claim 3, wherein in the step (A), the sample is further mixed with a phosphate buffer.

6. The method for measuring a concentration of creatinine in accordance with claim 5, wherein the phosphate buffer comprises a hydrogen phosphate and a dihydrogen phosphate.

7. The method for measuring a concentration of creatinine in accordance with clam 3, wherein in the step (A), the sample is further mixed with an electrolyte salt of a monovalent anion.

8. The method for measuring a concentration of creatinine in accordance with claim 7, wherein the monovalent anion is selected from the group consisting of a chloride ion, a nitrate ion, and a methyl sulfate ion.

9. The method for measuring a concentration of creatinine in accordance with claim 7, further comprising a molar amount of a phosphate buffer equal to or less than half the total of the molar amount of the electrolyte salt of a monovalent anion and the molar amount of the 1-methoxy-5-methylphenazinium.

10. The method for measuring a concentration of creatinine in accordance with claim 1,
wherein the step (B) includes the steps of:
(D) bringing the sample into contact with two or more electrodes and applying a voltage between the two electrodes; and
(E) detecting a current value or an amount of electric charge flowing between the two electrodes, and
in the step (C), the concentration of the creatinine contained in the sample is determined from the current value or the amount of electric charge detected in the step (E).

11. The method for measuring a concentration of creatinine in accordance with claim 1,
wherein the step (B) includes the steps of:
(F) irradiating the sample with light; and
(G) detecting the light transmitted through the sample or the light reflected by the sample, and
in the step (C), the concentration of the creatinine contained in the sample is determined from an intensity of the transmitted light or the reflected light detected in the step (G).

* * * * *